United States Patent
Dolzhenko et al.

(10) Patent No.: US 12,374,422 B2
(45) Date of Patent: Jul. 29, 2025

(54) SEQUENCE-GRAPH BASED TOOL FOR DETERMINING VARIATION IN SHORT TANDEM REPEAT REGIONS

(71) Applicant: Illumina, Inc., San Diego, CA (US)

(72) Inventors: Egor Dolzhenko, San Diego, CA (US); Michael A. Eberle, Oceanside, CA (US)

(73) Assignee: ILLUMINA, INC., San Diego, CA (US)

( * ) Notice: Subject to any disclaimer, the term of this patent is extended or adjusted under 35 U.S.C. 154(b) by 902 days.

(21) Appl. No.: 16/811,919

(22) Filed: Mar. 6, 2020

(65) Prior Publication Data

US 2020/0286586 A1     Sep. 10, 2020

Related U.S. Application Data

(60) Provisional application No. 62/815,322, filed on Mar. 7, 2019.

(51) Int. Cl.
| | |
|---|---|
| *G16B 20/20* | (2019.01) |
| *G06N 7/01* | (2023.01) |
| *G16B 5/20* | (2019.01) |
| *G16B 30/10* | (2019.01) |
| *G16B 40/00* | (2019.01) |

(52) U.S. Cl.
CPC .............. *G16B 20/20* (2019.02); *G06N 7/01* (2023.01); *G16B 5/20* (2019.02); *G16B 30/10* (2019.02); *G16B 40/00* (2019.02)

(58) Field of Classification Search
CPC ........ G16B 20/20; G16B 30/10; G16B 40/00; G16B 5/20; G06N 7/01
See application file for complete search history.

(56) References Cited

U.S. PATENT DOCUMENTS

| | | |
|---|---|---|
| 10,699,801 B2 | 6/2020 | Eberle et al. |
| 2014/0114582 A1 | 4/2014 | Mittelman et al. |
| 2015/0199474 A1 | 7/2015 | Kural |
| 2017/0249421 A1 | 8/2017 | Eberle et al. |
| 2020/0335178 A1 | 10/2020 | Eberle et al. |

FOREIGN PATENT DOCUMENTS

| | | |
|---|---|---|
| KR | 20210138556 A | 11/2021 |
| RU | 2263949 C2 | 11/2005 |
| RU | 2016139287 A | 5/2018 |
| RU | 2019100495 A | 1/2019 |
| WO | WO2013/041577 | 3/2013 |
| WO | WO-2013149385 A1 | 10/2013 |
| WO | WO 2015058120 A1 | 4/2015 |
| WO | WO 2016038220 A1 | 3/2016 |
| WO | WO-2017070096 A1 | 4/2017 |

OTHER PUBLICATIONS

Xu et al. "Decompositions of Multiple Breakpoint Graphs and Rapid Exact Solutions." Algorithms in Bioinformatics. WABI 2008. Lecture Notes in Computer Science. vol. 5251, pp. 25-37. (Year: 2008).*
Li et al. "A survey of sequence alignment algorithms for next-generation sequencing." Briefings in Bioinformatics. 2010. vol. 2(5), pp. 473-483. (Year: 2010).*
Szalkowski. "Fast and robust multiple sequence alignment with phylogeny-aware gap placement." BMC Bioinformatics. 2012. vol. 13(129), pp. 1-11. (Year: 2012).*
Szalkowski et al. "Graph-based modeling of tandem repeats improves global multiple sequence alignment." Nucleic Acids Research. 2013. vol. 41(17), pp. 1-11. (Year: 2013).*
Rand et al. "Coordinates and intervals in graph-based reference genomes." BMC Bioinformatics. 2017. vol. 18(263), pp. 1-8. (Year: 2017).*
Donev et al. "Recruitment of Heterogeneous Nuclear Ribonucleoprotein A1 in Vivo to the LMP/TAP Region of the Major Histocompatibility Complex." The Journal of Biological Chemistry. 2003. vol. 278(7), pp. 5214-5226. (Year: 2003).*
Pellegrini et al. "Tandem repeats discovery service (TReaDS) applied to finding novel cis-acting factors in repeat expansion diseases." BMC Bioinformatics. 2012. vol. 13(Suppl 4):S3, pp. 1-15. (Year: 2012).*
Treangen et al. "Repetitive DNA and next-generation sequencing: computational challenges and solutions." Nature Reviews: Genetics. 2012. vol. 13, pp. 36-46. (Year: 2012).*
Compeau et al. "How to apply de Bruijn graphs to genome assembly." Computational Biology, vol. 29, No. 11, pp. 987-991. (Year: 2011).*
Flicek et al. "Sense from sequence reads: methods for alignment and assembly." Nature Methods Supplement, vol. 6, No. 11S, pp. S6-S12. (Year: 2009).*
"Tool for Simulating Sequence Reads from a Reference Genome", https://github.com/lh3/wgsim., 2011, 1-2.
1000 Genomes Project, Consortium, "A global reference for human genetic variation", Nature 526, Oct. 1, 2015, 68-74.
Amiel, J., et al., "Polyalanine expansion and frameshift mutations of the paired-like homeobox gene PHOX2B in congenital central hypoventilation syndrome", Nature Genetics 33, 2003, 459-461.

(Continued)

*Primary Examiner* — Kaitlyn L Minchella
*Assistant Examiner* — Steven W. Bailey
(74) *Attorney, Agent, or Firm* — ILLUMINA, INC.

(57) ABSTRACT

The disclosed embodiments concern methods, apparatus, systems and computer program products for genotyping repeat sequences such as medically significant short tandem repeats (STRs). The methods involve aligning reads to a repeat sequence represented by a sequence graph, and using the aligned reads to genotype the repeat sequence. The sequence graph is a directed graph each including at least one self-loop representing a repeat sub-sequence. In some implementations, the reads are paired end reads, and both mates of each read pair may be used to genotype the repeat sequences. Some implementations can be used to determine degenerate codon repeats. Some implementations can be used to genotype repeat sequences each including two or more repeat sub-sequences. Some implementations can be used to genotype nucleic acid sequences each including at least one repeat sub-sequence and another genetic variant such as an insertion, deletion, or substitution.

23 Claims, 12 Drawing Sheets

Specification includes a Sequence Listing.

(56) References Cited

OTHER PUBLICATIONS

Benjamini, et al., "Summarizing and correcting the GC content bias in high-throughput sequencing", Nucleic Acids Research, Feb. 9, 2012, 1-14.
Cornish-Bowden, A., et al., "Nomenclature for incompletely specified bases in nucleic acid sequences: recommendations 1984.", Nucleic Acids Research 13(9), 1985, 3021-3030.
Dashnow, H., et al., "STRetch: detecting and discovering pathogenic short tandem repeat expansions", Genome Biology 19:191, Aug. 21, 2018, 1-13.
Dilthey, A., et al., "Improved genome inference in the MHC using a population reference graph", Nature Genetics 47, 2015, 682-688.
Doi, et al., "Rapid detection of expanded short tandem repeats in personal genomics using hybrud sequencing", Bioinformatics vol. 30, No. 6, Mar. 15, 2014, 815-822.
Dolzhenko, E., et al., "Detection of long repeat expansions from PCR-free whole-genome sequence data", Genome Res 27, Sep. 8, 2017, 1895-1903.
Dryland, et al., "Simple repeat-primed PCR analysis of the Myotonic Type 1 Gene in a clinical diagnostics environment", URL:http://www.hindawi.com/journals/jnd/2013/857564.
Froggatt, N., et al., "A common MSH2 mutation in English and North American HNPCC families: Origin, phenotypic expression, and sex specific differences in colorectal cancer", J. Med Genet 36(2), Feb. 1999, 97-102.
Garrison, E., et al., "Variation graph toolkit improves read mapping by representing genetic variation in the reference.", Nat Biotechnol 36(9), Oct. 2018, 875-879.
Gymrek, M., et al., "Abundant contribution of short tandem repeats to gene expression variation in humans", Nature Genetics 48, 2016, 22-29.
Hannan, A., et al., "Tandem repeats mediating genetic plasticity in health and disease.", Nat Rev Genetics 19(5), May 2018, 286-298.
Lee, C., et al., "Multiple sequence alignment using partial order graphs", Bioinformatics 18(3), Mar. 2002, 452-464.
Lee, J., et al., "Pathogenic Mechanisms of Myotonic Dystrophy", Biochemical Society Transactions 37(6), Nov. 19, 2009, 1281-86.
Li, H., et al., "Aligning Sequence Reads, Clone Sequences and Assembly Contigs with BWA-MEM", https://arxiv.org/abs/1303.3997, 2013, 1-3.
Lincoln, S., et al., "A Rigorous Interlaboratory Examination of the Need to Confirm Next-Generation Sequencing-Detected Variants with an Orthogonal Method in Clinical Genetic Testing", The Journal of Molecular Diagnostics 21(2), Mar. 2019, 318-329.
Mousavi, N., et al., "Profiling the genome-wide landscape of tandem repeat expansions", bioRxiv 361162; doi: https://doi.org/10.1101/361162, Jul. 3, 2018, 1-25.
Paten, B., et al., "Genome graphs and the evolution of genome inference", Genome Res, Mar. 14, 2017, 1-56.
Richards, R., "Dynamic mutations: a decade of unstable expanded repeats in human genetic disease", Oxford Univerity Press 10(20), 2001, 2187-2194.
Shoubridge, C., et al., "Polyalanine Tract Disorders and Neurocognitive Phenotypes.", Advances in Experimental Medicine and Biology 769, 2012, 185-203.
Tang, H., et al., "Profiling of Short-Tandem-Repeat Disease Alleles in 12,632 Human Whole Genomes", Am J Hum Genet 101(5), Nov. 2, 2017, 700-715.
Novak, P., et al., "RepeatExplorer: a Galaxy-based web server for genome-wide characterization of eukaryotic repetitive elements from next-generation sequence reads", Bioinformatics 29(6), Feb. 1, 2013, 792-793.
Novak, P., et al., "TAREAN: a computational tool for identification and characterization of satellite DNA from unassembled short reads", Nucleic Acids Research 45(12) e111, Apr. 10, 2017, 1-10.
PCT/US2020/021550, "International Search Report and Written Opinion", Jun. 3, 2020, 1-18.
RU Office Action dated Nov. 1, 2023, in Application No. RU2023116499 with English translation.
RU Office Action dated Oct. 24, 2022, in application No. RU2021108143 with English translation.
SG Office Action dated May 3, 2023, in application No. SG11202103205Q.
AU Office Action dated Jun. 3, 2022, in Application No. AU2021202149.
Cao, M.D., et al., "Inferring Short Tandem Repeat Variation From Paired-end Short Reads," Nucleic acids research, 2014, vol. 42(3), pp. 1-11.
Extended European search report dated Oct. 21, 2022, in Application No. EP22168725.4.
International Preliminary Report on Patentability dated Mar. 23, 2017 in Application No. PCT/EP2015/070902.
U.S. Non-Final office Action dated Jan. 11, 2019 in U.S. Appl. No. 15/510,219.
U.S. Non-Final Office Action dated Nov. 15, 2023 in U.S. Appl. No. 16/869,455.
U.S. Notice of Allowance dated Feb. 10, 2020 in U.S. Appl. No. 15/510,219.
U.S. Notice of Allowance dated Jun. 5, 2020 in U.S. Appl. No. 15/510,219.
U.S. Notice of Allowance dated May 28, 2020 in U.S. Appl. No. 15/510,219.

* cited by examiner

SEQUENCE-GRAPH BASED TOOL FOR DETERMINING VARIATION IN SHORT TANDEM REPEAT REGIONS

INCORPORATION BY REFERENCE

An Application Data Sheet is filed concurrently with this specification as part of the present application. Each application that the present application claims benefit of or priority to as identified in the concurrently filed Application Data Sheet is incorporated by reference herein in its entirety and for all purposes.

BACKGROUND

Repeat expansions are a special class of microsatellite and minisatellite variants involving short tandem repeat (STR) polymorphisms. Repeat expansions are also known as dynamic mutations due to their instability when short tandem repeats expand beyond certain sizes. Genetic disorders caused by unstable repeat expansions include, among others, fragile X syndrome (FXS), Huntington's disease, and amyotrophic lateral sclerosis (ALS).

Identifying repeat expansions is important in the diagnosis and treatment of certain genetic disorders. However, it is difficult to determine repeat sequences using short reads that do not fully traverse the repeat sequence. Therefore, it is desirable to develop methods using short reads to identify medically relevant repeat expansions.

SUMMARY

The disclosed implementations concern methods, apparatus, systems, and computer program products for sequencing genomic loci including repeat sequences such as short tandem repeat sequences, which may correlate with genetic disorders. The methods involve aligning reads to sequence graphs each representing a genomic locus, and using the aligned reads to genotype one or more repeat sequences in the genomic locus. The sequence graphs are directed graphs each including at least one self-loop representing a repeat sequence.

A first aspect of the disclosure provides computer-implemented methods for genotyping genomic loci including repeat sequences. The methods are implemented using a computer including one or more processors and system memory. The methods can be used to genotoype one or more repeat sequences each including one or more repeat sub-sequences. The methods include: (a) collecting, using the one or more processors, sequence reads of a test sample from a database; (b) aligning, by the one or more processors, the sequence reads to the one or more repeat sequences each represented by a sequence graph, wherein the sequence graph has a data structure of a directed graph with vertices representing nucleic acid sequences and directed edges connecting the vertices, and wherein the sequence graph includes one or more self-loops, each self-loop representing a repeat sub-sequence, each repeat sub-sequence comprising repeats of a repeat unit of one or more nucleotides; and (c) determining, by the one or more processors, one or more genotypes for the one or more repeat sequences using the sequence reads aligned to the one or more repeat sequences.

In some implementations, a repeat sequence of the one or more repeat sequences includes a particular repeat unit including at least one incompletely specified nucleotide. In some implementations, the particular repeat unit includes degenerate codons.

In some implementations, the one or more self-loops include two or more self-loops representing two or more repeat sub-sequences.

In some implementations, the sequence graph further includes two or more alternative paths for two or more alleles. In some implementations, the two or more alleles include an indel or a substitution. In some implementations, the substitution includes a single nucleotide variant (SNV) or a single nucleotide polymorphism (SNP). In some implementations, the method further includes genotyping the two or more alleles using sequence reads aligned to the two or more alternative paths. In some implementations, genotyping the two or more alleles includes providing coverages of the two or more alternative paths to a probabilistic model to determine the probabilities of the two or more alleles. In some implementations, the probabilistic model simulates a probability of an allele as a function of the coverage of the allele, the function being selected from a Poisson distribution, negative-binomial distribution, a binomial distribution, or a beta-binomial distribution. In some implementations, the Poisson distribution's rate parameter is estimated from read length and mean depth observed at the genomic locus.

In some implementations, the method further includes, aligning, before (b), the sequence reads to a reference genome to determine genomic coordinates of the sequence reads, and selecting a subset of sequence reads as the sequence reads to be aligned to the one or more repeat sequences each represented by a sequence graph. In some implementations, the subset of sequence reads includes reads aligned to or near a region represented by a sequence graph. In some implementations, the subset of sequence reads includes unaligned reads whose mates map to or near a region represented by a sequence graph. In some implementations, the subset of sequence reads includes reads aligned to one or more off-target regions that are known hot spots for misaligning reads.

In some implementations, aligning a sequence read to the sequence graph includes: finding a kmer match between the sequence read and a path of the sequence graph; and extending the kmer match to a full alignment of nodes and edges of the sequence graph including one or more self-loops.

In some implementations, aligning a sequence read to the sequence graph includes graph shrinking by removing low confidence ends of the alignments.

In some implementations, aligning a sequence read to the sequence graph includes alignment merging by: aligning subsequences of the read to a sequence graph; and merging alignments of the subsequences to form a full alignment of the sequence read.

In some implementations, the method further includes generating the sequence graph based on locus specification including a locus structure of the genomic locus.

In some implementations, the sequence reads include paired end reads, and operation (c) includes: (i) identifying anchor and anchored reads in the paired end reads, wherein the anchor reads are reads aligned to or near the one or more repeat sequences, and the anchored reads are unaligned reads that are paired with the anchor reads; and (ii) determining the one or more genotypes for the one or more repeat sequences using at least the anchored reads.

In some implementations, operation (ii) includes determining the one or more genotypes for the one or more repeat sequences using the anchor reads as well as the anchored reads. In some implementations, he anchor reads are aligned to within about 5 kb of a repeat sequence. In some implementations, the unaligned reads include reads that cannot be aligned or are poorly aligned to the sequence graph.

In some implementations, the one or more repeat sequences include a short tandem repeat (STR) sequence. In some implementations, an expansion of the STR is associated with Fragile X syndrome, amyotrophic lateral sclerosis (ALS), Huntington's disease, Friedreich's ataxia, spinocerebellar ataxia, spino-bulbar muscular atrophy, myotonic dystrophy, Machado-Joseph disease, or dentatorubral pallidoluysian atrophy.

In some implementations, the method further includes using a sequencer to generate paired end reads from the test sample.

In some implementations, the method further includes extracting the test sample from an individual.

In some implementations, the test sample is a blood sample, a urine sample, a saliva sample, or a tissue sample.

In some implementations, the repeat unit includes 1 to 50 nucleotides.

In some implementations, the reads are shorter than at least one of the one or more repeat sequences.

Another aspect of the disclosure provides systems for genotyping genomic loci including repeat sequences. In some implementations, the system includes: system memory and one or more processors configured to: (a) collect, using the one or more processors, sequence reads of a test sample from a database; (b) align, by the one or more processors, the sequence reads to the one or more repeat sequences each represented by a sequence graph, wherein the sequence graph has a data structure of a directed graph with vertices representing nucleic acid sequences and directed edges connecting the vertices, and wherein the sequence graph includes one or more self-loops, each self-loop representing a repeat sub-sequence, each repeat sub-sequence comprising repeats of a repeat unit of one or more nucleotides; and (c) determine, by the one or more processors, one or more genotypes for the one or more repeat sequences using the sequence reads aligned to the one or more repeat sequences.

In some implementations, the system also includes a sequencer for sequencing nucleic acids of a test sample.

In some implementation, the one or more processors are configured to perform various methods described herein.

Another aspect of the disclosure provides a computer program product including a non-transitory machine readable medium storing program code that, when executed by one or more processors of a computer system, causes the computer system to implement the methods above for genotyping genomic loci including repeat sequences. The program code includes, (a) code for collecting sequence reads of a test sample from a database; (b) code for aligning the sequence reads to the one or more repeat sequences each represented by a sequence graph, wherein the sequence graph has a data structure of a directed graph with vertices representing nucleic acid sequences and directed edges connecting the vertices, and wherein the sequence graph comprises one or more self-loops, each self-loop representing a repeat sub-sequence, each repeat sub-sequence comprising repeats of a repeat unit of one or more nucleotides; and (c) code for determining one or more genotypes for the one or more repeat sequences using the sequence reads aligned to the one or more repeat sequences.

In some implementations, the program code includes code for performing operations of methods described herein.

Although the examples herein concern humans and the language is primarily directed to human concerns, the concepts described herein are applicable to genomes from any plant or animal. These and other objects and features of the present disclosure will become more fully apparent from the following description and appended claims, or may be learned by the practice of the disclosure as set forth hereinafter.

DETAILED DESCRIPTION

Figure 1A:
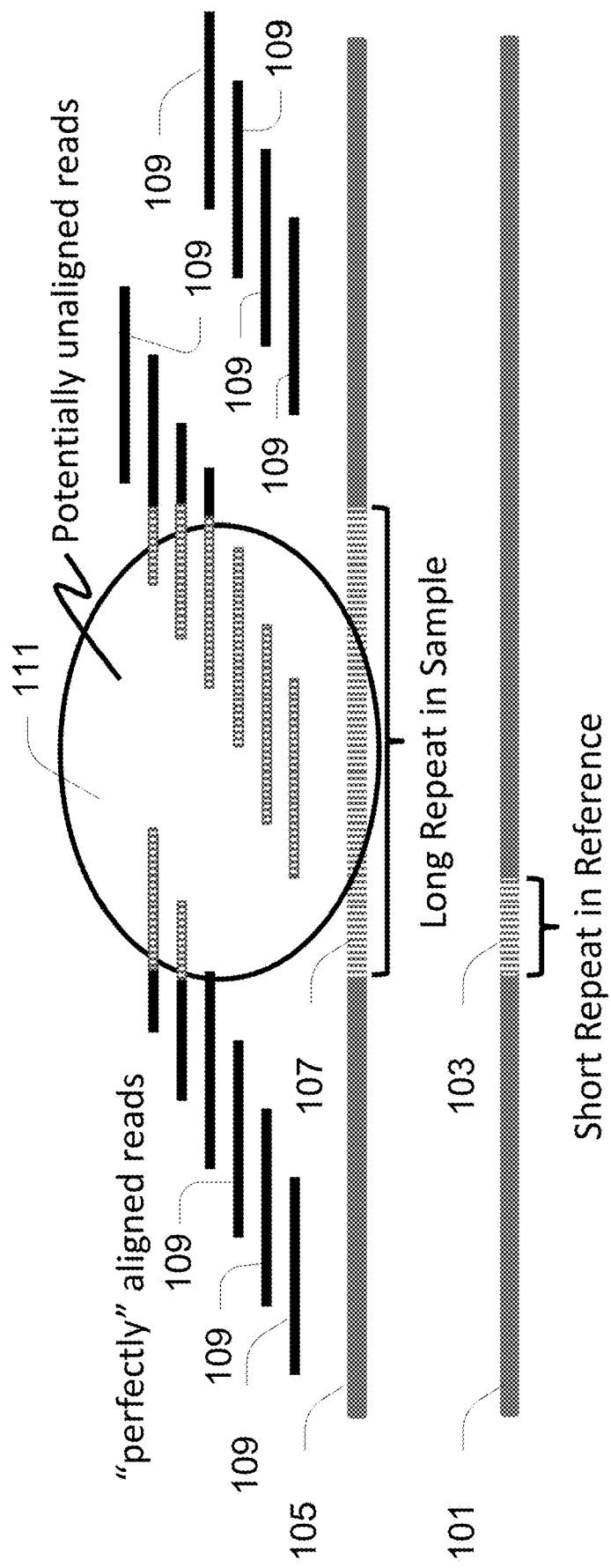
FIG. 1A is a schematic diagram illustrating difficulties in alignment of sequence reads to a repeat sequence on a reference sequence.

The disclosure concerns methods, apparatus, systems, and computer program products for identifying repeat expansions of interest, such as expansions of repeat sequences that are medically significant. Examples of repeat expansions include but are not limited to expansions associated with genetic disorders such as Fragile X syndrome, ALS, Huntington's disease, Friedreich's ataxia, spinocerebellar ataxia, spino-bulbar muscular atrophy, myotonic dystrophy, Machado-Joseph disease, and dentatorubral pallidoluysian atrophy.

Unless otherwise indicated, the practice of the methods and systems disclosed herein involves conventional techniques and apparatus commonly used in molecular biology, microbiology, protein purification, protein engineering, protein and DNA sequencing, and recombinant DNA fields that are within the skill of the art. Such techniques and apparatus are known to those of skill in the art and are described in numerous texts and reference works (See e.g., Sambrook et al., "Molecular Cloning: A Laboratory Manual," Third Edition (Cold Spring Harbor), [2001]); and Ausubel et al., "Current Protocols in Molecular Biology" [1987]).

Numeric ranges are inclusive of the numbers defining the range. It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The headings provided herein are not intended to limit the disclosure.

Unless defined otherwise herein, all technical and scientific terms used herein have the same meaning as commonly understood by one of ordinary skill in the art. Various scientific dictionaries that include the terms included herein are well known and available to those in the art. Although any methods and materials similar or equivalent to those described herein find use in the practice or testing of the embodiments disclosed herein, some methods and materials are described.

The terms defined immediately below are more fully described by reference to the Specification as a whole. It is to be understood that this disclosure is not limited to the particular methodology, protocols, and reagents described, as these may vary, depending upon the context they are used by those of skill in the art.

Definitions

As used herein, the singular terms "a," "an," and "the" include the plural reference unless the context clearly indicates otherwise.

Unless otherwise indicated, nucleic acids are written left to right in 5' to 3' orientation and amino acid sequences are written left to right in amino to carboxy orientation, respectively.

The term "plurality" refers to more than one element. For example, the term is used herein in reference to a number of nucleic acid molecules or sequence reads that is sufficient to identify significant differences in repeat expansions in test samples and control samples using the methods disclosed herein.

The term "repeat sequence" refers to a nucleic acid sequence including repetitive occurrences of a shorter sequence. The shorter sequence is referred to as a "repeat unit" herein. The repetitive occurrences of the repeat unit are referred to as "repeats" or "copies" of the repeat unit. In many contexts, the location of a repeat sequence is associated with a gene encoding a protein. In other situations, a repeat sequence may be in a non-coding region. The repeat units may occur in the repeat sequence with or without breaks between the repeat units. For instance, in normal samples, the FMR1 gene tends to include an AGG break in the CGG repeats, e.g., (CGG)10+(AGG)+(CGG)9. Samples lacking a break, as well as long repeat sequences having few breaks, are prone to repeat expansion of the associated gene, which can lead to genetic diseases as the repeats expand above a particular number. In various embodiments of the disclosure, the number of repeats is counted as in-frame repeats regardless of breaks. Methods for estimating in-frame repeats are further described hereinafter.

In various embodiments, the repeat units include 1 to 100 nucleotides. Many repeat units widely studied are trinucleotide or hexanucleotide units. Some other repeat units that have been well studied and are applicable to the embodiments disclosed herein include but are not limited to units of 4, 5, 6, 8, 12, 33, or 42 nucleotides. See, e.g., Richards (2001) Human Molecular Genetics, Vol. 10, No. 20, 2187-2194. Applications of the disclosure are not limited to the specific number of nucleotide bases described above, so long as they are relatively short compared to the repeat sequence having multiple repeats or copies of the repeat units. For example, a repeat unit can include at least 3, 6, 8, 10, 15, 20, 30, 40, 50 nucleotides. Alternatively or additionally, a repeat unit can include at most about 100, 90, 80, 70, 60, 50, 40, 30, 20, 10, 6 or 3 nucleotides.

A repeat sequence may be expanded in evolution, development, and mutagenic conditions, creating more copies of the same repeat unit. This is referred to as "repeat expansion" in the field. This process is also referred to as "dynamic mutation" due to the unstable nature of the expansion of the repeat unit. Some repeat expansions have been shown to be associated with genetic disorders and pathological symptoms. Other repeat expansions are not well understood or studied. The disclosed methods herein may be used to identify both previously known and new repeat expansions. In some embodiments, a repeat sequence having a repeat expansion is longer than about 100, 150, 300 or 500 base pairs (bp). In some embodiments, a repeat sequence having the repeat expansion is longer than about 1000 bp, 2000 bp, 3000 bp, 4000 bp, 5000 bp, or 10000 bp etc.

In graph theory, vertex and edge are the two basic units out of which graphs are constructed. A vertex or node is one of the points on which a graph is defined and which may be connected by edges. In a diagram of a graph, a vertex can be represented by a shape with a label, and an edge is represented by a line (undirected edge) or arrow (directed edge) extending from one vertex to another.

The two vertices connected by an edge are said to be the endpoints of the edge. A vertex x is said to be adjacent to another vertex y if the graph contains an edge (x, y).

An undirected graph consists of a set of vertices and a set of undirected edges (connecting unordered pairs of vertices), while a directed graph consists of a set of vertices and a set of directed edges (connecting ordered pairs of vertices).

In graph theory, each edge has two (or in hypergraphs, more) vertices to which it is attached, called its endpoints. Edges may be directed or undirected; undirected edges are also called lines and directed edges are also called arcs or arrows.

A directed edge is an edge that connects an upstream vertex and a downstream vertex, wherein the upstream vertex appears before the directed edge and the downstream vertex appears after the directed edge.

An undirected edge is an edge that connects two vertices, wherein either vertex can appear before the other in a graph path.

Loops, self-loops, and single-node loops are used interchangeably herein. A loop has one node and an edge with both ends connected to the one node.

A cycle is a path including two or more vertices, wherein the path of the cycle starts and ends with a same vertex. A simple cycle is a cycle that does not have repeated vertices or edges other than the start and end vertex.

A cyclic graph is a graph that includes at least one cycle.

An acyclic graph is a graph that does not include any cycles or self-loops.

A directed acyclic graph (DAG) is a directed graph without any cycles or self-loops.

A graph path is a sequence of vertices and edges, wherein both endpoints of an edge appear adjacent to the edge in the sequence. A graph path of a directed graph has an upstream vertex appearing before a directed edge (or arc or arrow) and a downstream vertex appearing after the directed edge.

A Poisson distribution is a discrete probability distribution that expresses the probability of a given number of events occurring in a fixed interval of time or space if these events occur with a known constant rate and independently of the time since the last event.

Completely specified base symbols include G, A, T, C for guanine, adenine, thymine, and cytosine, respectively.

Incompletely specified nucleic acid nomenclature include, inter alia, as follows.

Purine (adenine or guanine): R
Pyrimidine (thymine or cytosine): Y
Adenine or thymine: W
Guanine or cytosine: S
Adenine or cytosine: M
Guanine or thymine: K
Adenine or thymine or cytosine: H
Guanine or cytosine or thymine: B
Guanine or adenine or cytosine: V
Guanine or adenine or thymine: D
Guanine or adenine or thymine or cytosine: N The term "paired end reads" refers to reads obtained from paired end sequencing that obtains one read from each end of a nucleic fragment. Paired end sequencing involves fragmenting DNA into sequences called inserts. In some protocols such as some used by Illumina, the reads from shorter inserts (e.g., on the order of tens to hundreds of bp) are referred to as short-insert paired end reads or simply paired end reads. In contrast, the reads from longer inserts (e.g., on the order of several thousands of bp) are referred to as mate pair reads. In this disclosure, short-insert paired end reads and long-insert mate pair reads may both be used and are not differentiated with regard to the process for analyzing repeat expansions. Therefore, the term "paired end reads" may refer to both short-insert paired end reads and long-insert mate pair reads, which are further described herein after. In some embodiments, paired end reads include reads of about 20 bp to 1000 bp. In some embodiments, paired end reads include reads of about 50 bp to 500 bp, about 80 bp to 150 bp, or about 100 bp. It will be understood that the two reads in a paired end need not be located at the extreme end of the fragment that is sequenced. Rather, one or both read can be proximate to the end of the fragment. Furthermore, methods exemplified herein in the context of paired end reads can be carried out with any of a variety of paired reads independent of whether the reads are derived from the end of a fragment or other part of a fragment.

As used herein, the terms "alignment" and "aligning" refer to the process of comparing a read to a reference sequence and thereby determining whether the reference sequence contains the read sequence. An alignment process attempts to determine if a read can be mapped to a reference sequence, but does not always result in a read aligned to the reference sequence. If the reference sequence contains the read, the read may be mapped to the reference sequence or, in certain embodiments, to a particular location in the reference sequence. In some cases, alignment simply tells whether or not a read is a member of a particular reference sequence (i.e., whether the read is present or absent in the reference sequence). For example, the alignment of a read to the reference sequence for human chromosome 13 will tell whether the read is present in the reference sequence for chromosome 13. A tool that provides this information may be called a set membership tester. In some cases, an alignment additionally indicates a location in the reference sequence where the read maps to. For example, if the reference sequence is the whole human genome sequence, an alignment may indicate that a read is present on chromosome 13, and may further indicate that the read is on a particular strand and/or site of chromosome 13.

Aligned reads are one or more sequences that are identified as a match in terms of the order of their nucleic acid molecules to a known reference sequence such as a reference genome. An aligned read and its determined location on the reference sequence constitute a sequence tag. Alignment can be done manually, although it is typically implemented by a computer algorithm, as it would be impossible to align reads in a reasonable time period for implementing the methods disclosed herein. One example of an algorithm from aligning sequences is the Efficient Local Alignment of Nucleotide Data (ELAND) computer program distributed as part of the Illumina Genomics Analysis pipeline. Alternatively, a Bloom filter or similar set membership tester may be employed to align reads to reference genomes. See U.S. patent application Ser. No. 14/354,528, filed Apr. 25, 2014, which is incorporated herein by reference in its entirety. The matching of a sequence read in aligning can be a 100% sequence match or less than 100% (i.e., a non-perfect match).

The term "mapping" used herein refers to assigning a read sequence to a larger sequence, e.g., a reference genome, by alignment.

In some instances one end read of two paired end reads is aligned to a repeat sequence of a reference sequence, while the other end read of the two paired end reads is unaligned. In such instances, the paired read that is aligned to a repeat sequence of a reference sequence is referred to as an "anchor read." A paired end read unaligned to the repeat sequence but is paired with the anchor read is referred to as an anchored read. As such, an unaligned read can be anchored to and associated with the repeat sequence. In some embodiments, the unaligned reads include both reads that cannot be aligned to the reference sequence and reads that are poorly aligned to a reference sequence. When a read is aligned to a reference sequence with a number of mismatched bases above a certain criterion, the read is considered poorly aligned. For example, in various embodiments, a read is considered poorly aligned when it is aligned with at least about 1, 2, 3, 4, 5, 6, 7, 8, 9 or 10 mismatches. In some instances, both reads of a pair are aligned to a reference sequence. In such instances, both reads may be analyzed as "anchor reads" in various implementations.

The terms "polynucleotide," "nucleic acid" and "nucleic acid molecules" are used interchangeably and refer to a covalently linked sequence of nucleotides (i.e., ribonucleotides for RNA and deoxyribonucleotides for DNA) in which the 3' position of the pentose of one nucleotide is joined by a phosphodiester group to the 5' position of the pentose of the next. The nucleotides include sequences of any form of nucleic acid, including, but not limited to RNA and DNA molecules such as cell-free DNA (cfDNA) molecules. The term "polynucleotide" includes, without limitation, single- and double-stranded polynucleotides.

The term "test sample" herein refers to a sample, typically derived from a biological fluid, cell, tissue, organ, or organism, that includes a nucleic acid or a mixture of nucleic acids having at least one nucleic acid sequence that is to be screened for copy number variation. In certain embodiments the sample has at least one nucleic acid sequence whose copy number is suspected of having undergone variation. Such samples include, but are not limited to sputum/oral fluid, amniotic fluid, blood, a blood fraction, or fine needle biopsy samples, urine, peritoneal fluid, pleural fluid, and the like. Although the sample is often taken from a human subject (e.g., a patient), the assays can be used to copy number variations (CNVs) in samples from any mammal, including, but not limited to dogs, cats, horses, goats, sheep, cattle, pigs, etc. The sample may be used directly as obtained from the biological source or following a pretreatment to modify the character of the sample. For example, such pretreatment may include preparing plasma from blood, diluting viscous fluids, and so forth. Methods of pretreatment may also involve, but are not limited to, filtration, precipitation, dilution, distillation, mixing, centrifugation, freezing, lyophilization, concentration, amplification, nucleic acid fragmentation, inactivation of interfering components, the addition of reagents, lysing, etc. If such methods of pretreatment are employed with respect to the sample, such pretreatment methods are typically such that the nucleic acid(s) of interest remain in the test sample, sometimes at a concentration proportional to that in an untreated test sample (e.g., namely, a sample that is not subjected to any such pretreatment method(s)). Such "treated" or "processed" samples are still considered to be biological "test" samples with respect to the methods described herein.

A control sample may be a negative or positive control sample. A "negative control sample" or "unaffected sample" refers to a sample including nucleic acids that is known or expected to have a repeat sequence having a number of repeats within a range that is not pathogenic. A "positive control sample" or "affected sample" is known or expected to have a repeat sequence having a number of repeats within a range that is pathogenic. Repeats of the repeat sequence in a negative control sample typically have not been expanded beyond a normal range, whereas repeats of a repeat sequence in a positive control sample typically have been expanded beyond a normal range. As such, the nucleic acids in a test sample can be compared to one or more control samples.

The term "sequence of interest" herein refers to a nucleic acid sequence that is associated with a difference in sequence representation in healthy versus diseased individuals. A sequence of interest can be a repeat sequence on a chromosome that is expanded in a disease or genetic condition. A sequence of interest may be a portion of a chromosome, a gene, a coding or non-coding sequence.

The term "Next Generation Sequencing (NGS)" herein refers to sequencing methods that allow for massively parallel sequencing of clonally amplified molecules and of single nucleic acid molecules. Non-limiting examples of NGS include sequencing-by-synthesis using reversible dye terminators, and sequencing-by-ligation.

The term "parameter" herein refers to a numerical value that characterizes a physical property. Frequently, a parameter numerically characterizes a quantitative data set and/or a numerical relationship between quantitative data sets. For example, a ratio (or function of a ratio) between the number of sequence tags mapped to a chromosome and the length of the chromosome to which the tags are mapped, is a parameter.

The term "call criterion" herein refers to any number or quantity that is used as a cutoff to characterize a sample such as a test sample containing a nucleic acid from an organism suspected of having a medical condition. The threshold may be compared to a parameter value to determine whether a sample giving rise to such parameter value suggests that the organism has the medical condition. In certain embodiments, a threshold value is calculated using a control data set and serves as a limit of diagnosis of a repeat expansion in an organism. In some implementations, if a threshold is exceeded by results obtained from methods disclosed herein, a subject can be diagnosed with a repeat expansion. Appropriate threshold values for the methods described herein can be identified by analyzing values calculated for a training set of samples or control samples. Threshold values can also be calculated from empirical parameters such as sequencing depth, read length, repeat sequence length, etc. Alternatively, affected samples known to have repeat expansion can also be used to confirm that the chosen thresholds are useful in differentiating affected from unaffected samples in a test set. The choice of a threshold is dependent on the level of confidence that the user wishes to have to make the classification. In some embodiments, the training set used to identify appropriate threshold values comprises at least 10, at least 20, at least 30, at least 40, at least 50, at least 60, at least 70, at least 80, at least 90, at least 100, at least 200, at least 300, at least 400, at least 500, at least 600, at least 700, at least 800, at least 900, at least 1000, at least 2000, at least 3000, at least 4000, or more qualified samples. It may be advantageous to use larger sets of qualified samples to improve the diagnostic utility of the threshold values.

The term "read" refers to a sequence read from a portion of a nucleic acid sample. Typically, though not necessarily, a read represents a short sequence of contiguous base pairs in the sample. The read may be represented symbolically by the base pair sequence (in ATCG) of the sample portion. It may be stored in a memory device and processed as appropriate to determine whether it matches a reference sequence or meets other criteria. A read may be obtained directly from a sequencing apparatus or indirectly from stored sequence information concerning the sample. In some cases, a read is a DNA sequence of sufficient length (e.g., at least about 25 bp) that can be used to identify a larger sequence or region, e.g., that can be aligned and mapped to a chromosome or genomic region or gene.

The term "genomic read" is used in reference to a read of any segments in the entire genome of an individual.

The term "site" refers to a unique position (i.e. chromosome ID, chromosome position and orientation) on a reference genome. In some embodiments, a site may be a residue, a sequence tag, or a segment's position on a sequence.

As used herein, the term "reference genome" or "reference sequence" refers to any particular known genome sequence, whether partial or complete, of any organism or virus which may be used to reference identified sequences from a subject. For example, a reference genome used for human subjects as well as many other organisms is found at the National Center for Biotechnology Information at ncbi.nlm.nih.gov. A "genome" refers to the complete genetic information of an organism or virus, expressed in nucleic acid sequences.

In various embodiments, the reference sequence is significantly larger than the reads that are aligned to it. For example, it may be at least about 100 times larger, or at least about 1000 times larger, or at least about 10,000 times larger, or at least about $10^5$ times larger, or at least about $10^6$ times larger, or at least about $10^7$ times larger.

In one example, the reference sequence is that of a full length human genome. Such sequences may be referred to as genomic reference sequences. In another example, the reference sequence is limited to a specific human chromosome such as chromosome 13. In some embodiments, a reference Y chromosome is the Y chromosome sequence from human genome version hg19. Such sequences may be referred to as chromosome reference sequences. Other examples of reference sequences include genomes of other species, as well as chromosomes, sub-chromosomal regions (such as strands), etc., of any species.

In some embodiments, a reference sequence for alignment may have a sequence length from about 1 to about 100 times the length of a read. In such embodiments, the alignment and sequencing are considered a targeted alignment or sequencing, instead of a whole genome alignment or sequencing. In these embodiments, the reference sequence typically include a gene and/or a repeat sequence of interest.

In various embodiments, the reference sequence is a consensus sequence or other combination derived from multiple individuals. However, in certain applications, the reference sequence may be taken from a particular individual.

The term "clinically-relevant sequence" herein refers to a nucleic acid sequence that is known or is suspected to be associated or implicated with a genetic or disease condition. Determining the absence or presence of a clinically-relevant sequence can be useful in determining a diagnosis or confirming a diagnosis of a medical condition, or providing a prognosis for the development of a disease.

The term "derived" when used in the context of a nucleic acid or a mixture of nucleic acids, herein refers to the means whereby the nucleic acid(s) are obtained from the source from which they originate. For example, in one embodiment, a mixture of nucleic acids that is derived from two different genomes means that the nucleic acids, e.g., cfDNA, were naturally released by cells through naturally occurring processes such as necrosis or apoptosis. In another embodiment, a mixture of nucleic acids that is derived from two different genomes means that the nucleic acids were extracted from two different types of cells from a subject.

The term "based on" when used in the context of obtaining a specific quantitative value, herein refers to using another quantity as input to calculate the specific quantitative value as an output.

The term "patient sample" herein refers to a biological sample obtained from a patient, i.e., a recipient of medical attention, care or treatment. The patient sample can be any of the samples described herein. In certain embodiments, the patient sample is obtained by non-invasive procedures, e.g., peripheral blood sample or a stool sample. The methods described herein need not be limited to humans. Thus, various veterinary applications are contemplated in which case the patient sample may be a sample from a non-human mammal (e.g., a feline, a porcine, an equine, a bovine, and the like).

The term "biological fluid" herein refers to a liquid taken from a biological source and includes, for example, blood, serum, plasma, sputum, lavage fluid, cerebrospinal fluid, urine, semen, sweat, tears, saliva, and the like. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

As used herein, the term "corresponding to" sometimes refers to a nucleic acid sequence, e.g., a gene or a chromosome, that is present in the genome of different subjects, and which does not necessarily have the same sequence in all genomes, but serves to provide the identity rather than the genetic information of a sequence of interest, e.g., a gene or chromosome.

As used herein the term "chromosome" refers to the heredity-bearing gene carrier of a living cell, which is derived from chromatin strands comprising DNA and protein components (especially histones). The conventional internationally recognized individual human genome chromosome numbering system is employed herein.

As used herein, the term "polynucleotide length" refers to the absolute number of nucleic acid monomer subunits (nucleotides) in a sequence or in a region of a reference genome. The term "chromosome length" refers to the known length of the chromosome given in base pairs, e.g., provided in the NCBI36/hg18 assembly of the human chromosome found at lgenomel.lucscl.ledu/cgi-bin/hgTracks?hgsid=167155613&chromInfoPage= on the World Wide Web.

The term "subject" herein refers to a human subject as well as a non-human subject such as a mammal, an invertebrate, a vertebrate, a fungus, a yeast, a bacterium, and a virus. Although the examples herein concern humans and the language is primarily directed to human concerns, the concepts disclosed herein are applicable to genomes from any plant or animal, and are useful in the fields of veterinary medicine, animal sciences, research laboratories and such.

The term "primer," as used herein refers to an isolated oligonucleotide that is capable of acting as a point of initiation of synthesis when placed under conditions inductive to synthesis of an extension product (e.g., the conditions include nucleotides, an inducing agent such as DNA polymerase, and a suitable temperature and pH). The primer may be preferably single stranded for maximum efficiency in amplification, but alternatively may be double stranded. If double stranded, the primer is first treated to separate its strands before being used to prepare extension products. The primer may be an oligodeoxyribonucleotide. The primer is sufficiently long to prime the synthesis of extension products in the presence of the inducing agent. The exact lengths of the primers will depend on many factors, including temperature, source of primer, use of the method, and the parameters used for primer design.

Introduction

Short tandem repeats (STRs) are ubiquitous throughout the human genome. Although our understanding of STR biology is far from complete, emerging evidence suggests that STRs play an important role in basic cellular processes.

Repeat expansions are a special class of microsatellite and minisatellite variants involving STR polymorphisms. Repeat expansions are also known as dynamic mutations due to their instability when short tandem repeats expand beyond certain sizes. STR expansions are a major cause of over 20 severe neurological disorders including amyotrophic lateral sclerosis, Friedreich ataxia (FRDA), Huntington's disease (HD), and fragile X syndrome. Table 1 exemplifies a small number of pathogenic repeat expansions that are different from repeat sequences in normal samples. The columns show genes associated with the repeat sequences, the nucleic acid sequences of the repeat units, the numbers of repeats of the repeat units for normal and pathogenic sequences, and the diseases associated with the repeat expansions.

TABLE 1

Examples of pathogenic repeat expansions

| Gene | Repeat | Normal | Pathogenic | Disease |
| --- | --- | --- | --- | --- |
| FMR1 | CGG | 6-60 | 200-900 | Fragile X |
| AR | CAG | 9-36 | 38-62 | Spino-bulbar muscular atrophy |
| GHTT | CAG | 11-34 | 40-121 | Huntington's disease |
| FXN | GAA | 6-32 | 200-1700 | Fredreich's ataxia |
| ATXN1 | CAG | 6-39 | 40-82 | Spinocerebellar ataxia |
| ATXN10 | ATTCT | 10-20 | 500-4500 | Spinocerebellar ataxia |
| ATXN2 | CAG | 15-24 | 32-200 | Spinocerebellar ataxia |
| ATXN3 | CAG | 13-36 | 61-84 | Spinocerebellar ataxia |
| ATXN7 | CAG | 4-35 | 37-306 | Spinocerebellar ataxia |
| C9ofr72 | GGGGCC | <30 | 100's | ALS |

Genetic disorders involving repeat expansions are heterogeneous in many respects. The size of the repeat unit, degree of expansion, location with respect to the affected gene, and pathogenic mechanism may vary from disorder to disorder. For example, ALS involves a hexanucleotide repeat expansion of the nucleotides GGGGCC in the C9orf72 gene located on the short arm of chromosome 9 open reading frame 72. In contrast, Fragile X syndrome is associated with the expansion of the CGG trinucleotide repeat (triplet repeat) affecting the Fragile X mental retardation 1 (FMR1) gene on the X chromosome. An expansion of the CGG repeats can result in a failure to express the fragile X mental retardation protein (FMRP), which is required for normal neural development. Depending on the length of the CGG repeat, an allele may be classified as normal (unaffected by the syndrome), a pre-mutation (at risk of fragile X associated disorders), or full mutation (usually affected by the syndrome). According to various estimates, there are from 230 to 4000 CGG repeats in mutated FMR1 genes that cause fragile X syndrome in affected patients, as compared with 60 to 230 repeats in carriers prone to ataxia, and 5 to 54 repeats in unaffected individuals. Repeat expansion of the FMR1 gene is a cause for autism, as about 5% of autistic individuals are found to have the FMR1 repeat expansion. McLennan, et al. (2011), Fragile X Syndrome, Current Genomics 12 (3): 216-224. A definitive diagnosis of fragile X syndrome involves genetic testing to determine the number of CGG repeats.

Various general properties of repeat expansion related diseases have been identified in multiple studies. Repeat expansion or dynamic mutation is usually manifested as an increase in repeat number, with mutation rate being related to the number of repeats. Rare events such as loss of repeat interruption can lead to alleles having an increased likelihood of expanding, with such events being known as founder events. There may be a relationship between the number of repeats in the repeat sequence and the severity and/or onset of the disease caused by repeat expansion.

Therefore, identifying and calling repeat expansions is important in the diagnosis and treatment of various diseases. However, identifying repeat sequences, especially using reads that do not fully traverse the repeat sequence, has various challenges. First, it is difficult to align repeats to a reference sequence because there is not a clear one-to-one mapping between the read and the reference genome. Additionally, even if a read is aligned to a reference sequence, the reads are often too short to fully cover a medically relevant repeat sequence. For instance, the reads may be about 100 bp. In comparison, a repeat expansion can span hundreds to thousands of base pairs. In fragile X syndrome, for example, the FMR1 gene can have well over 1000 repeats, spanning over 3000 bp. So a 100-bp read cannot map the full length of the repeat expansion. Moreover, assembling short reads into a longer sequence may not overcome the short read versus long repeat problem, because it is difficult to assemble short reads into a longer sequence due to the ambiguous alignment of repeats in one read with repeats on another read.

Alignment is the primary culprit for loss of information either due to incompleteness of the reference sequence, non-unique correspondence between a read and sites on the reference sequence, or significant deviations from the reference sequence. Systematic sequencing errors and other issues affecting read accuracy are a secondary factor for failure in detecting repeat sequences. In some experimental protocols, about 7% reads are unaligned or with a MAPQ score of 0. Even as researchers work to improve sequencing technology and analysis tools, there will always be a significant amount of unalignable and poorly aligned reads. Implementations of the methods herein rely on unalignable or poorly aligned reads to identify repeat expansions.

Methods using long reads to detect repeat expansion have their own challenges. In next generation sequencing, currently available technologies using longer reads are slower and more error prone than technologies using shorter reads. Moreover, long reads are not feasible for some applications, such as sequencing cell-free DNA. Cell-free DNA obtained in maternal blood can be used for pre-natal genetic diagnosis. The cell-free DNA exists as fragments typically shorter than 200 bp. As such, methods using long reads are not feasible for pre-natal genetic diagnosis using cell-free DNA. Implementations of the methods described herein use short reads to identify repeat expansions that are medically relevant.

Moreover, conventional methods are not designed to handle complex loci that harbor multiple repeats. Important examples of such loci include the CAG repeat that causes HD flanked by a CCG repeat, the GAA repeat that causes FRDA flanked by an adenosine homopolymer, and the CAG repeat that causes Spinocerebellar ataxia type 8 (SCAB) flanked by an ACT repeat. An even more extreme example is the CCTG repeat in the CNBP gene whose expansions cause Myotonic Dystrophy type 2 (DM2). This repeat is adjacent to polymorphic TG and TCTG repeats (J. E. Lee and Cooper 2009) making it particularly difficult to accurately align reads to this locus. Another type of complex repeat is the polyalanine repeat which has been associated with at least nine disorders to date (Shoubridge and Gecz 2012). Polyalanine repeats consist of repetitions of α-amino acid codons GCA, GCC, GCG, or GCT.

Clusters of variants can affect alignment and genotyping accuracy (Lincoln et al. 2019). Variants adjacent to low complexity polymorphic sequences can be additionally problematic because methods for variant discovery can output clusters of inconsistently represented or spurious variant calls in such genomic regions. This, in part, is due to the elevated error rates of such regions in sequencing data (Benjamini and Speed 2012; Dolzhenko et al. 2017). One example is a single-nucleotide variant (SNV) adjacent to an adenosine homopolymer in MSH2 that causes Lynch syndrome I (Froggatt et al. 1999).

Implementations disclosed herein can handle complex loci as described above. They use sequence graph as a general and flexible model of each target locus.

In some implementations, the disclosed methods address aforementioned challenges in identifying and calling repeat expansions by utilizing paired end sequencing. Paired end sequencing involves fragmenting DNA into sequences called inserts. In some protocols such as some used by Illumina, the reads from shorter inserts (e.g. on the order of tens to hundreds of bp) are referred to as short-insert paired end reads or simply paired end reads. In contrast, the reads from longer inserts (e.g., on the order of several thousands of bp) are referred to as mate pair reads. As noted above, short-insert paired end reads and long-insert mate pair reads may both be used in various implementations of the methods disclosed herein.

FIG. 1A is a schematic illustration showing certain difficulties in aligning sequence reads to a repeat sequence on a reference sequence, especially when aligning sequence reads obtained from a sample of a long repeat sequence having a repeat expansion. At the bottom of FIG. 1A is a reference sequence 101 having a relatively short repeat sequence 103 illustrated by vertical hatch lines. In the middle of figure is a hypothetical sequence 105 of a patient sample having a long repeat sequence 107 harboring a repeat expansion, also illustrated by vertical hatch lines. Illustrated at the top of the figure are sequence reads 109 and 111 shown at locations of corresponding sites of the sample sequence 105. In some of these sequence reads, e.g., reads 111, some base pairs originate from the long repeat sequence 107, as illustrated also by vertical hatch lines and highlighted in a circle. Reads 111 having these repeats are potentially difficult to align to the reference sequence 101, because the repeats do not have clear corresponding locations on the reference sequence 101. Because these potentially unaligned reads cannot be clearly associated with the repeat sequence 103 in the reference sequence 101, it is difficult to obtain information regarding the repeat sequence and the expansion of the repeat sequence from these potentially unaligned reads 111. Furthermore, because these reads tend to be shorter than the long repeat sequence 107 harboring the repeat expansion, they cannot directly provide definitive information about the identity or location of the repeat sequence 107. Additionally, the repeats in the reads 111 make them difficult to assemble due to their ambiguous corresponding locations on the reference sequence 101 and the ambiguous relation amongst the reads 111. The reads that come partly from the long repeat sequence 107 in the sample, those illustrated as half hatched and half solid-black, may be aligned by the bases originating from outside of the repeat sequence 107. If the reads have too few base pairs outside of the repeat sequence 107, the reads may be poorly aligned or may not be aligned. So some of these reads with partial repeats may be analyzed as anchor reads, and others analyzed as anchored reads as further described below.

Figure 1B:
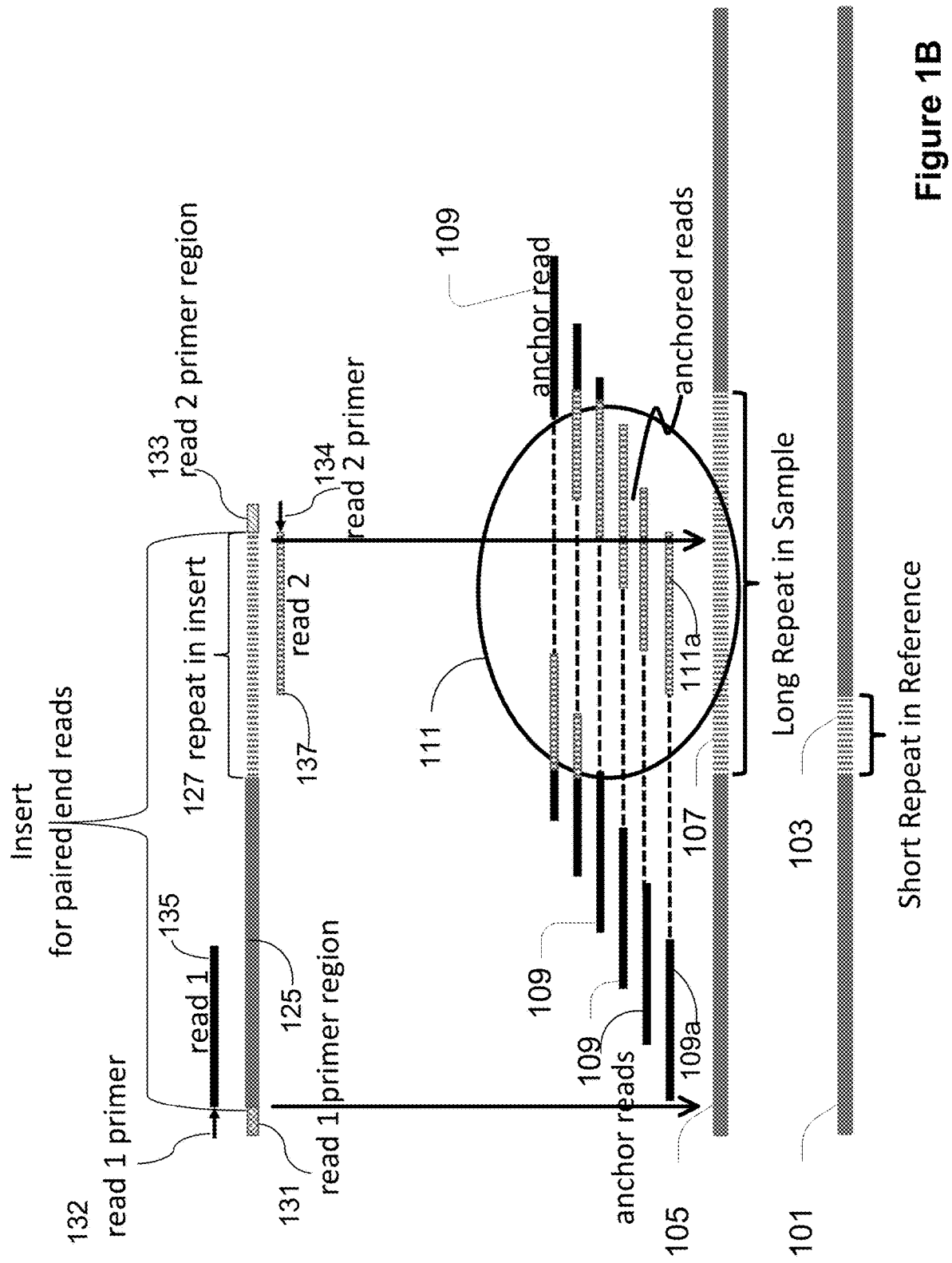
FIG. 1B is a schematic diagram illustrating alignment of sequence reads using paired end reads according to certain disclosed implementations to overcome the difficulties shown in FIG. 1A.

FIG. 1B is a schematic diagram illustrating how paired end reads may be utilized in some disclosed embodiments to overcome the difficulties shown in FIG. 1A. In paired end sequencing, sequencing occurs from both ends of fragments of nucleic acids in a test sample. Illustrated at the bottom of FIG. 1B are a reference sequence 101 and a sample sequence 105, as well as reads 109 and 111 equivalent to those shown in FIG. 1A. Illustrated at the top of FIG. 1B is a fragment 125 derived from a test sample sequence 105 and a read 1 primer region 131 and a read 2 primer region 133 for obtaining two reads 135 and 137 of the paired end reads. The fragment 125 is also referred to as an insert for the paired end reads. In some embodiments, inserts may be amplified with or without PCR. Some repeat sequences, such as those including a large number of GC or GCC repeats, cannot be sequenced well with traditional methods that include PCR amplification. For such sequences, amplification might be PCR-free. For other sequences, amplification may be performed with PCR.

The insert 125 illustrated in FIG. 1B corresponds to, or is derived from, a section of the sample sequence 105 flanked by two vertical arrows illustrated at the lower half of the figure. Specifically, the insert 125 harbors a repeat section 127 corresponding to part of the long repeat 107 in the sample sequence 105. The length of inserts may be adjusted for various applications. In some embodiments, the inserts may be somewhat shorter than the repeat sequence of interest or the repeat sequence having the repeat expansion. In other embodiments, the inserts may have a similar length to the repeat sequence or the repeat sequence having a repeat expansion. In yet further embodiments, the inserts may even be somewhat longer than the repeat sequence or the repeat sequence having the repeat expansion. Such inserts may be long inserts for mate pair sequencing in some embodiments further described below. Typically, the reads obtained from the inserts are shorter than the repeat sequence. Because inserts are longer than reads, paired end reads can better capture signals from a longer stretch of repeat sequence in the sample than single end reads.

The illustrated insert 125 has two read primer regions 131 and 133 at two ends of the insert. In some embodiments, read primer regions are inherent to the insert. In other embodiments, the primer regions are introduced to the insert by ligation or extension. Illustrated on the left end of the insert is a read 1 primer region 131, which allows the hybridization of a read 1 primer 132 to the insert 125. The extension of the read 1 primer 132 generates a first read, or read 1, labeled as 135. Illustrated on the right end of the insert 125 is a read 2 primer region 133, which allows the hybridization of a read 2 primer 134 to the insert 125, initiating the second read, or read 2, labeled as 137. In some embodiments, the insert 125 may also include index barcode regions (not shown in the figure here), providing a mechanism to identify different samples in a multiplex sequencing process. In some embodiments, the paired end reads 135 and 137 may be obtained by Illumina's sequencing by synthesis platforms. An example of a sequencing process implemented on such a platform is further described hereinafter in the Sequencing Methods Section, which process creates two paired end reads and two index reads.

The paired end reads obtained as illustrated in FIG. 1B may then be aligned to the reference sequence 101 having a relatively short repeat sequence 103. As such, the relative location and direction of a pair of reads are known. This allows an unalignable or poorly aligned read such as those shown in circle 111 to be indirectly associated with the relatively long repeat sequence 107 in the sample sequence 105 through the read's corresponding paired read 109 as seen at the bottom of FIG. 1B. In an illustrative example, the reads obtained from paired end sequencing are about 100 bp and the inserts are about 500 bp. In this example setup, the relative locations of the two paired end reads are about 300 base pairs apart from their 3' ends, and they have opposite directions. The relationship between the read pairs allows one to better associate reads to repeat regions. In some cases, a first read in a pair aligns with a non-repeat sequence flanking the repeat region on a reference sequence, and the second read in the pair does not properly align to the reference. See, for example, the pair of reads 109a and 111a illustrated in the bottom half of FIG. 1B, with the left one 109a of the pair being the first read, and the right one 111a being the second read. Given the pairing of the two reads 109a and 111a, the second read 111a can be associated with the repeat region 107 in the sample sequence 105, despite the fact that the second read 111a cannot be aligned to the reference sequence 101. Knowing the distance and direction of the second read 111a relative to the first read 109a, one can further determine the location of the second read 111a within the long repeat region 107. If a break exists among repeats in the second read 111a, the break's location relative to the reference sequence 101 may also be determined. A read such as the left read 109a that is aligned to the reference is referred to as an anchor read in this disclosure. A read such as the right one 111a that is not aligned to the reference sequence but is paired with an anchor read is referred to as an anchored read. As such, an unaligned sequence can be anchored to and associated with the repeat expansion. In this manner one can use short reads to detect long repeat expansions. While the challenge of detecting repeat expansions typically increases with the length of the expansion due to increased difficulty of sequencing, the methods disclosed herein can detect a higher signal from longer repeat expansion sequences than from shorter repeat expansion sequences. This is so because as the repeat sequence or repeat expansion gets longer, more reads will be anchored to the expansion region, more reads can fall completely in the repeat region, and more repeats can occur per read.

In some embodiments, the disclosed methods involve analyzing the frequency distribution of the numbers of repeats found in the anchor and anchored reads. In some embodiments, only the anchored reads are analyzed. In other embodiments, both the anchor and anchored reads are analyzed. The distribution of a test sample may be compared to an empirically or theoretically derived criterion separating unaffected samples from affected samples. In this way one may determine whether or not the test sample has the repeat expansion under consideration, and make a clinically relevant call.

The methods and apparatus described herein may employ next generation sequencing technology (NGS), which allows massively parallel sequencing. In certain embodiments, clonally amplified DNA templates or single DNA molecules are sequenced in a massively parallel fashion within a flow cell (e.g., as described in Volkerding et al. Clin Chem 55:641-658 [2009]; Metzker M Nature Rev 11:31-46 [2010]). The sequencing technologies of NGS include but are not limited to pyrosequencing, sequencing-by-synthesis with reversible dye terminators, sequencing by oligonucleotide probe ligation, and ion semiconductor sequencing. DNA from individual samples can be sequenced individually (i.e., singleplex sequencing) or DNA from multiple samples can be pooled and sequenced as indexed genomic molecules (i.e., multiplex sequencing) on a single sequencing run, to generate up to several hundred million reads of DNA sequences. Examples of sequencing technologies that can be used to obtain the sequence information according to the present method are further described below.

Various repeat expansion analyses using DNA samples involve aligning or mapping sequence reads from a sequencer to a reference sequence. A reference sequence may be the sequence of a whole genome, the sequence of a chromosome, the sequence of a sub-chromosomal region, etc. From a computational perspective, repeats create ambiguities in alignment, which, in turn, can produce biases and errors even at the whole chromosome counting level. Paired end reads coupled with adjustable insert length in various embodiments can help to eliminate ambiguity in alignment of repeating sequences and detection of repeat expansion.

Genotyping Variants at a Repeat Sequence Locus Using Sequence Graph

Figure 1C:
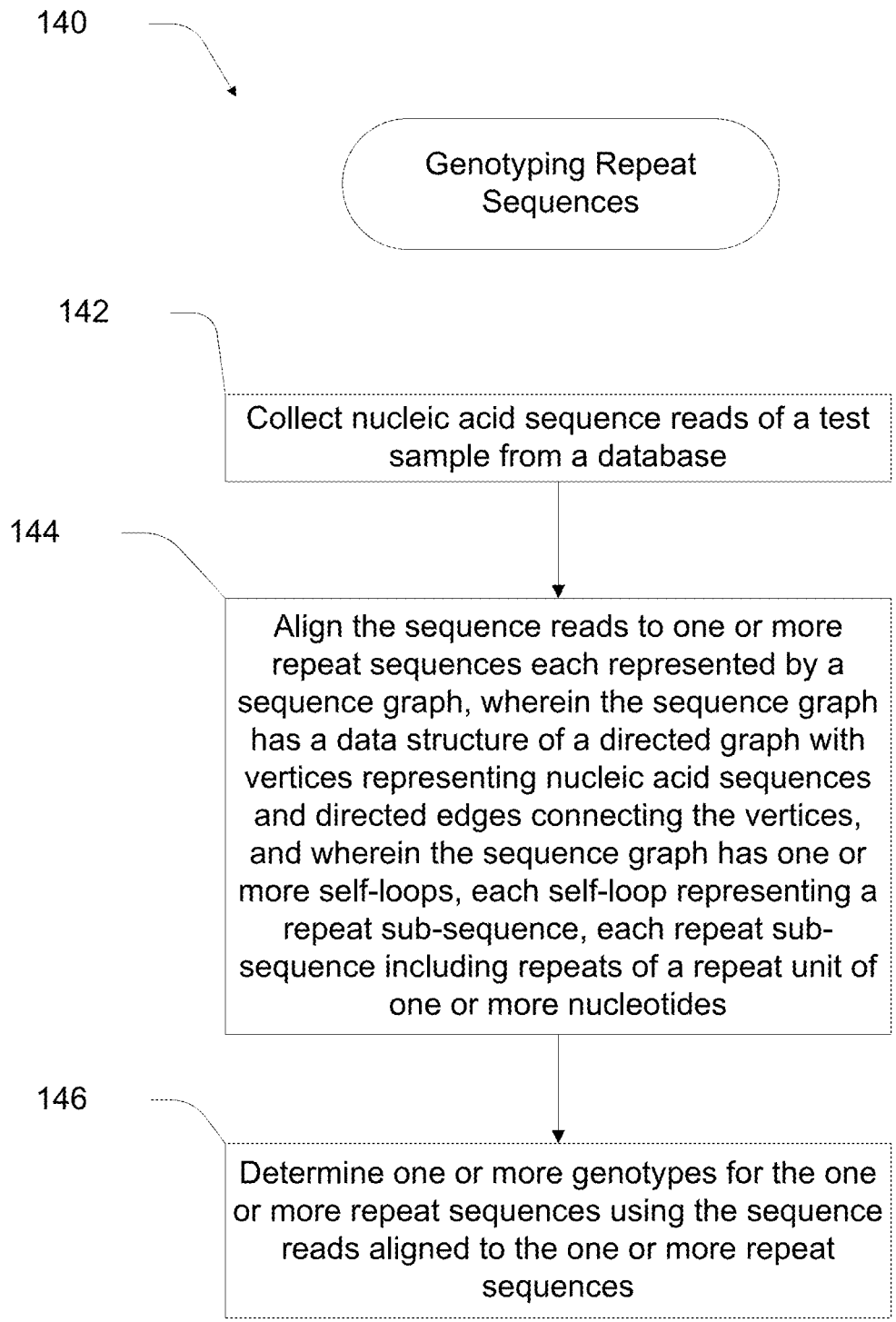
FIG. 1C shows a flowchart illustrating a process for genotyping a genomic locus including a repeat sequence according to some implementations.
Figure 1D:
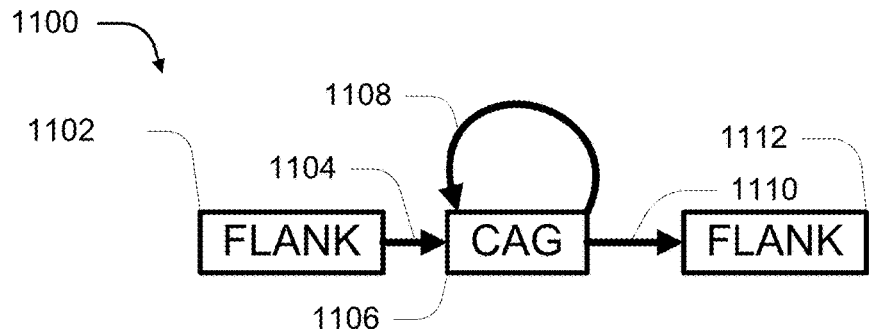
FIG. 1D shows a first sequence graph representing a first genomic locus.
Figure 1E:
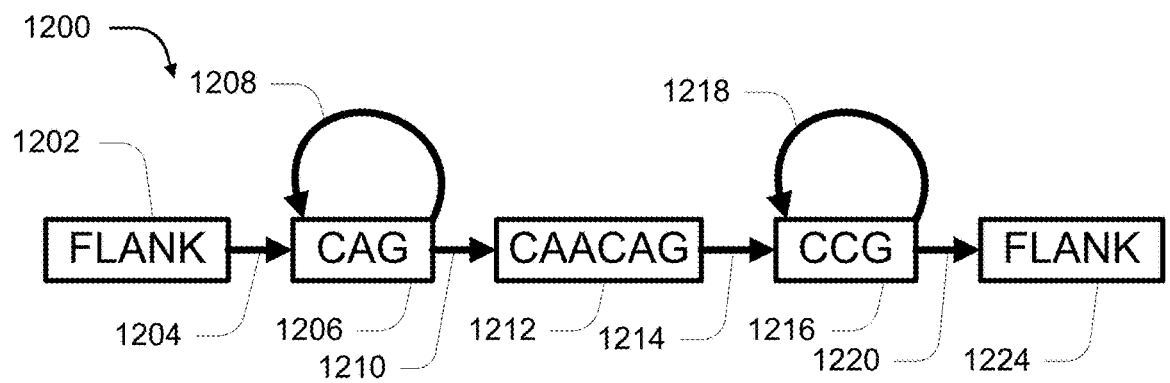
FIG. 1E shows a second sequence graph representing a second genomic locus.
Figure 1F:
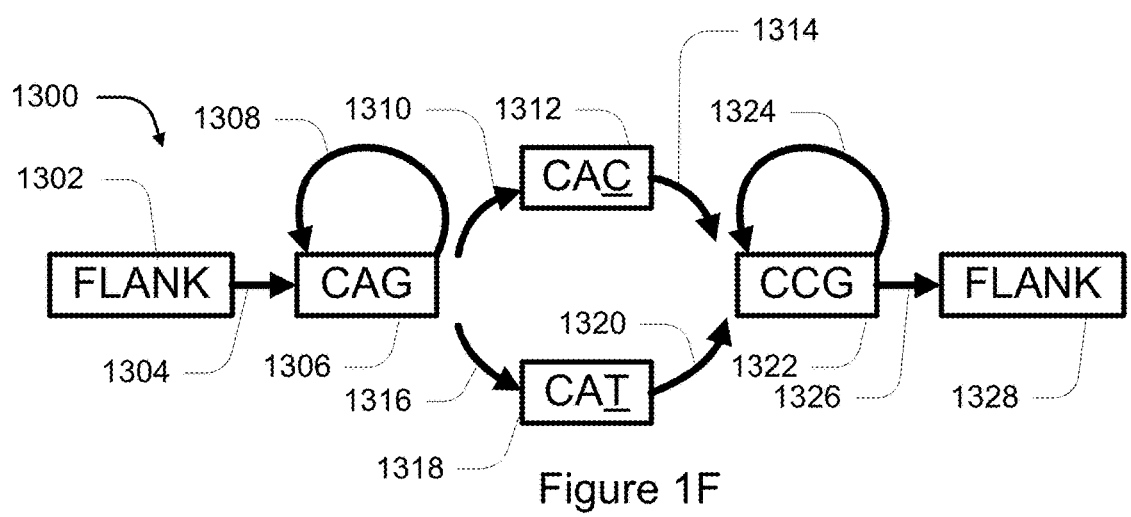
FIG. 1F shows a third sequence graph representing a third genomic locus.

FIG. 1C shows a flowchart illustrating process 140 for genotyping a genomic locus including a repeat sequence according to some implementations. In some implementations, the genetic locus is predefined in a variant catalog containing genomic locations and the structure of loci at the genomic locations. FIGS. 1D, 1E and 1F show three different sequence graphs according to some implementations.

Figure 1G:
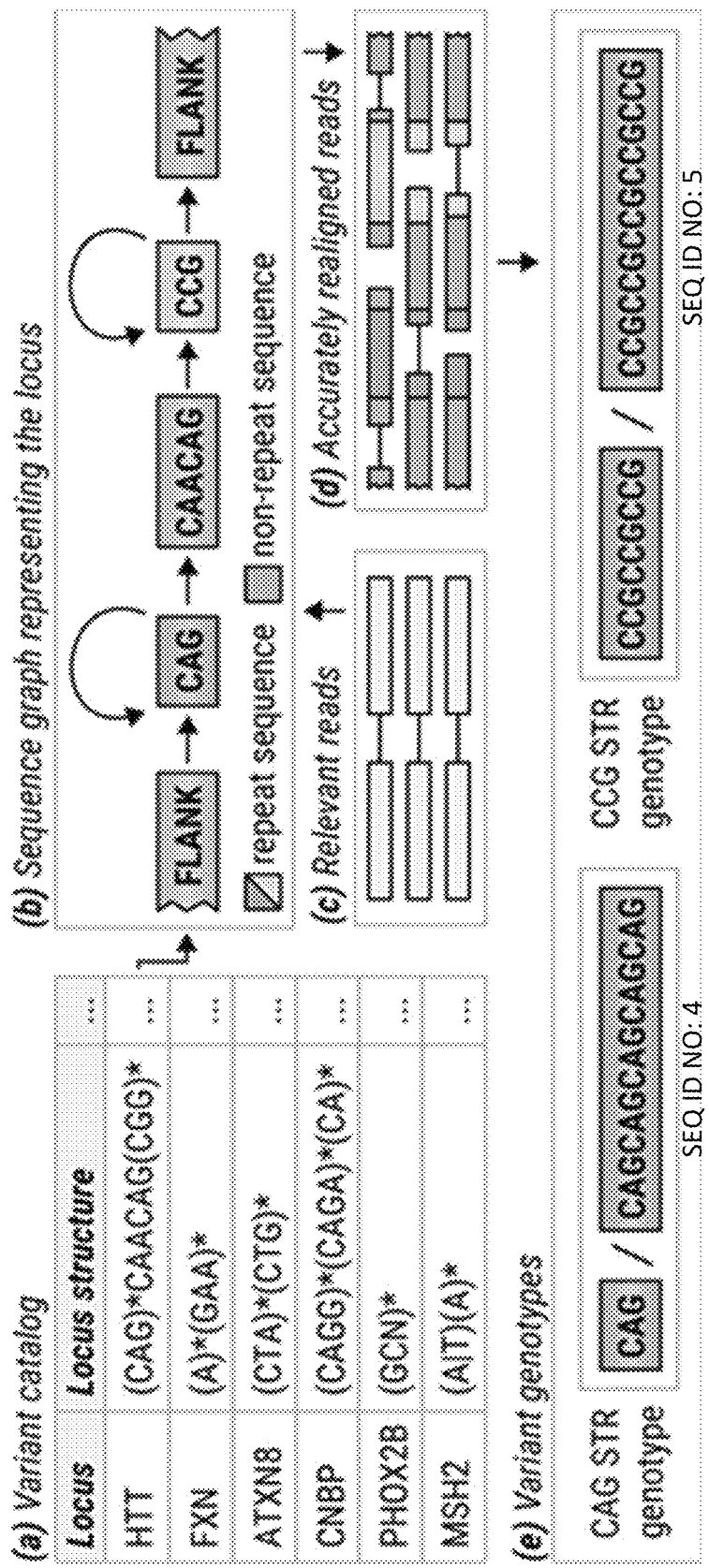
FIG. 1G shows a schematic diagram of a process for determining genotypes of variants at an HTT locus including two STR sequences according to some implementations.

FIG. 1G shows a schematic diagram of a process for determining genotypes of variants at an HTT locus including two STR sequences according to some implementations. FIG. 1G panel (a) illustrates a part of a variant catalog including genomic loci and their structure as locus specifications. For example, ignoring repeats, the sequence at locus HTT is CAGCAACAGCGG (SEQ ID NO: 2); the sequence at locus CNBP is CAGGCAGACA (SEQ ID NO: 3).

Figure 1H:
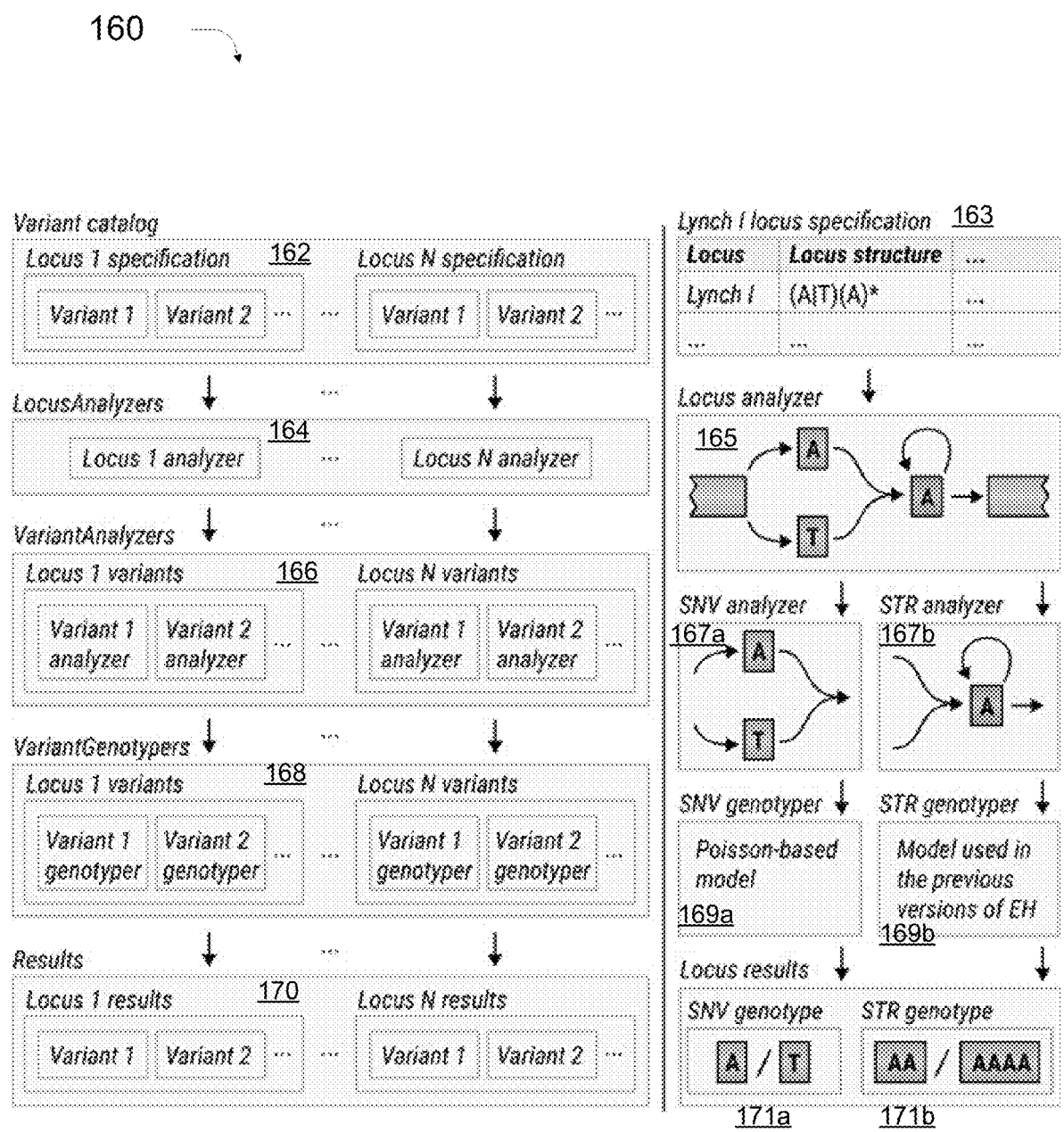
FIG. 1H shows a schematic diagram of a process for determining genotypes of variants at an Lynch I locus including a SNV and an STR according to some implementations. Left panel of FIG. 1H shows a schematic diagram of a general process for targeted genotyping; right panel shows an application of this process to genotyping variants at a locus associated with Lynch I syndrome.

FIG. 1H shows a schematic diagram of a process for determining genotypes of variants at a Lynch I locus including a SNV and an STR according to some implementations. FIG. 1H box 162 shows general structure of locus specifications, and box 163 shows a specific example of the locus specification of Lynch I (MSH2).

In the variant catalogue, the locus structure is specified using a restricted subset of the regular expression syntax. For example, the repeat region linked to HD can be defined by expression (CAG)*CAACAG(CGG)* or SEQ ID NO: 2 (ignoring repeats) that signifies that it harbors variable numbers of the CAG and CCG repeats separated by a CAACAG interruption; the region linked to the FRDA region corresponds to expression (A)*(GAA)*; the region linked to SCA8 corresponds to (CTA)*(CTG)*; the DM2 repeat region consisting of three adjacent repeats is defined by (CAGG)*(CAGA)*(CA)* or SEQ ID NO: 3 (ignoring repeats); the MSH2 SNV adjacent to an A homopolymer that causes Lynch syndrome I corresponds to (AIT)(A)*.

Additionally, the regular expressions are allowed to contain multi-allelic or "degenerate" base symbols that can be specified using the International Union of Pure and Applied Chemistry (IUPAC) notation ("Nomenclature for Incompletely Specified Bases in Nucleic Acid Sequences. Recommendations 1984. Nomenclature Committee of the International Union of Biochemistry (NC-IUB)" 1986).

Incompletely specified bases corresponding to bases in degenerate codons are referred to as degenerate bases herein. Degenerate bases make it possible to represent certain classes of imperfect DNA repeats where, for example, different bases may occur at the same position. Using this notation, polyalanine repeats can be encoded by the expression (GCN)* and polyglutamine repeats can be encoded by the expression (CAR)*.

In some implementations, the repeat sequence included in the genomic locus includes the short tandem repeat (STR) sequence. In some implementations, an extension of the FTR is associated with Fragile X syndrome, amyotrophic lateral sclerosis (ALS), Huntington's disease, Friedreich's ataxia, spinocerebellar ataxia, spino-bulbar muscular atrophy, myotonic dystrophy, Machado-Joseph disease, or dentatorubral pallidoluysian atrophy.

Process 140 involves collecting nucleic acid sequence reads of the test sample from a database. See block 142. In some implementations, the nucleic acid sequence reads have been initially aligned to a reference genome, but the process here realigns the sequence reads to the genomic locus of interest as explained below. In alternative implementations, reads can be directly aligned to the sequence graph without being initially aligned to the reference genome.

Process 140 involves aligning the sequence reads to a sequence for a genomic locus including one or more repeat sequences. See block 144. The sequence of a genomic locus is represented by data stored in the system memory having a data structure of a sequence graph. The sequence graph includes a directed graph with vertices representing nucleic acid sequences and directed edges connecting the vertices. The nucleic acid sequence in a vertex includes one or more nucleic acid bases. The sequence graph includes one or more self-loops. Each self-loop represents a repeat sequence of one or more repeat sequences. Each repeat sequence includes repeats of a repeat unit of one or more nucleotides.

In some implementations, sequence reads are initially aligned to a reference genome to determine the genomic coordinates of the reads before a subset of the initially aligned reads are aligned to one or more sequence graphs representing one or more sequence of interests. In some implementations, initially aligned reads are aligned to sequence graphs to determine repeat expansions at a few dozen to many thousands of regions (each region corresponding to a sequence graph). The total number of initially aligned reads that are realigned to sequence graphs during each invocation of an implementation can range from thousands to many millions of reads.

In some implementations, reads that are initially aligned to or near a sequence or locus of interest are selected as a subset of reads, which subset is then aligned to repeat sequences each represented by a sequence graph, the sequence graph having one or more self-loops representing one or more repeat sequences. In various implementations, a read within about 10, 50, 100, 500, 1,000, 2,000, 3,000, 4,000, 5,000, 6,000, 7,000, 8,000, 9,000, 10,000, 50,000, 100,000 bases from the sequence or locus of interest are considered near the sequence or locus of interest. In some implementations, a read within about 1,000, 2,000, 3,000, 4,000, 5,000, 6,000, 7,000, 8,000, 9,000, or 10,000 bases from the locus of interest are near the locus of interest. Some of the raw reads might have poor initial alignment because, e.g., they include repeat sequences that are hard to align unambiguously. In some implementations, reads that have poor initial alignment (e.g., as measured by an alignment score) but are each paired with a read aligned to or near the locus of interest (in a pair-end read pair) are aligned to the sequence graph. In some implementations, reads initially aligned to off-target regions that are known hot spots for misaligning reads are aligned to the sequence graph.

FIGS. 1D, 1E and 1F show three different sequence graphs according to some implementations. FIG. 1D shows a first sequence graph 1100 representing a first genomic locus including a repeat sequence having a trinucleotide repeat unit CAG. The first sequence graph 1100 includes vertices 1102 and 1112 respectively representing two franking sequences. The first sequence graph also includes vertex 1106 representing a repeat sequence including a trinucleotide repeat unit CAG. The first sequence graph includes a directed edge 1104 connecting vertex 1102 (flanking sequence) and vertex 1106 (CAG repeat sequence), the direction goes from vertex 1102 to vertex 1106. The direction of an edge indicates the relative position of two nucleic acid sequences. The first sequence graph also includes a directed edge 1104 connecting vertex 1102 (flanking sequence) and vertex 1106 (CAG repeat sequence), the direction goes from vertex 1102 to vertex 1106. The first sequence graph also includes a directed edge 1110 connecting vertex 1106 (CAG repeat sequence) and vertex 1112 (flanking sequence), the direction goes from vertex 1106 to vertex 1112. The first sequence graph also includes a self-loop 1108, which represents that a repeat sequence includes a repeat unit CAG (shown in vertex 1106) that repeats one or more times. A path going from the starting vertex to an ending vertex of a sequence graph represents the sequence of the genomic locus, which may include nucleotides near the repeat sequence such as flanking sequences.

FIG. 1E shows a second sequence graph 1200 representing a second genomic locus. The second sequence graph 1200 includes vertices 1202 and 1224 respectively representing two franking sequences. The second sequence graph also includes vertex 1206 and vertex 1216 respectively representing a repeat sequence including a trinucleotide repeat unit CAG and a repeat sequence including a trinucleotide repeat unit CCG, respectively. The second sequence graph further includes vertex 1212 representing a non-repeating sequence CAACAG. The second sequence graph includes directed edges 1204, 1210, 1214, and 1220. These directed edges directionally connect vertices 1202, 1206, 1212, 1216, and 1224 as illustrated. The second sequence graph also includes self-loop 1208, which represents that a repeat sequence includes a repeat unit CAG (shown in vertex 1206) that repeats one or more times. The second sequence graph also includes self-loop 1218, which represents that a repeat sequence includes a repeat unit CCG (shown in vertex 1216) that repeats one or more times.

FIG. 1F shows a third sequence graph 1300 representing a third genomic locus. The third sequence graph 1300 is similar to the second sequence graph 1200, but includes two alternative paths representing two alleles CAC and CAT. The two alleles may be alleles of SNV or SNP. Directed edge 1310, vertex 1312, and directed edge 1314 represent a first allele of CAC. Directed edge 1316, vertex 1318, and directed edge 1320 represent a second allele of CAT. The third sequence graph includes elements that are otherwise similar to those in the second sequence graph, including vertices 1302, 1306, 1322, and 1328. It also includes self-loops 1308 and 1324 indicating repeat sequences CAG repeats and CCG repeats. It further includes directed edges 1304 and 1326.

In some implementations, sequence reads are aligned to a sequence graph using techniques described as follows.

1. A kmer index is built on the entire graph such that given a kmer from the sequence one can enumerate all graph nodes at which such kmer begins or ends. In some instances a kmer can begin on one node and end on another node.

2. For each graph hit, extract two sub-graphs: one in the forward direction of the kmer and one in the reverse direction. The sub-graphs unroll repeat expansions up to the remaining read length and not include any nodes that are further away from the kmer hit than the remaining read length assuming repeats are not expanded. The procedure is a breadth first search and produces the data structure containing the following:

The concatenation of all node sequences (including expanded repeats) in the subgraph The index for the nodes so that it is easy to get the node id from the offset in a sequence when backtracking on smith-waterman algorithm For each node start offset, a sequence of offsets of the ends of the nodes that have edges incoming The index for each node such that it is easy to figure out whether the base is at the start of the node or not at the start of the node, and enumerate all the end offsets of the predecessor nodes.

3. Alignment:

Supports affine gaps.

Finds the best-scored alignment(s) for a sequence given the information above and the penalty matrix.

Two difference interfaces are available:

Best alignment and second best alignment score are reported.

The entire array of best alignments and the and second best alignment score.

The alignments are global alignments that penalize for the gap between the candidate kmer and the beginning of the aligned sequence. Some implementations tweak compile-time parameters.

Current algorithm for matrix filling is available in two implementations:

Sequential loops with N*M complexity.

Sequential loops of fixed-size loops of fixed length compile-time parameter defaulting to 16 which gcc automatically recognizes and translates into SSE or AVX vector instructions on CPU.

In some implementations, a particular repeat unit of a repeat sequence of the one or more repeat sequences includes at least one incompletely specified nucleotide. In some implementations, the particular repeat unit includes degenerate codons.

In some implementations, the one or more self-loops include two or more self-loops representing two or more repeat sequences. See, e.g., FIG. 1E, FIG. 1F, and FIG. 1G panel (b).

In some implementations, the sequence graph further includes two or more alternative paths for two or more alleles. See, e.g., FIG. 1F, reference numbers 1312 and 1318. See also FIG. 1H, reference numbers 165, and 167a for locus Lynch I (MSH2), where an upper path includes a vertex for nucleic acid base A, and a lower path includes a vertex for nucleic acid base T.

In some implementations, the two or more alleles include an indel or a substitution. In some implementations, the substitution includes a single nucleotide variant (SNV) or a single nucleotide polymorphism (SNP). See, e.g., FIG. 1F, reference numbers 1312 and 1318.

In some implementations, aligning a sequence read to the sequence graph includes: finding a kmer match between the sequence read and a path of the sequence graph and then extending this path to a full alignment. In some implementations, the aligning includes extracting a subgraph around the path; unrolling any loops in the subgraph to obtain a directional acyclic graph; and performing a Smith-Waterman alignment of the sequence read against the directional acyclic graph.

In some implementations, aligning a sequence read to the sequence graph includes graph shrinking by removing low confidence ends of the alignments. After a read was aligned to a graph, the method searches for other similar alternative alignments. This is done by realigning the original read to paths through the graph that overlap the path of the original alignment. This allows detecting if, e.g., one or both ends of the initial alignment have low confidence, which indicates that they could have been aligned in a different way. Being able to detect high and low confidence parts of the alignment allows one to accurately determine which genetic variants the read supports.

In some implementations, aligning a sequence read to the sequence graph includes alignment merging by: aligning subsequences of the read to a sequence graph; and merging alignments of the subsequences to form a full alignment of the sequence read.

In some implementations, the process also involves generating the sequence graph based on locus specification including a locus structure of the genomic locus. In some implementations, the locus specification is defined in a variant catalogue as explained above.

See also FIG. 1G panels (b)-(d) for schematic illustrations of alignment of reads to a sequence graph for the HTT locus.

FIG. 1H reference schematically illustrates locus analyzers 164 for performing alignment of reads to a sequence graph, such as for the locus Lynch I (165).

Process 140 further involves determining one or more genotypes for the one or more repeat sequences using sequence reads aligned to the sequence graph. See block 140. See also FIG. 1G panel (e) illustrating determining two STRs (CAG and CCG) at the HTT locus. The sequence on the left including repeats of CAG is CAGCAGCAGCAGCAG (SEQ ID NO: 4). The sequence on the left including repeats of CCG is CCGCCGCCGCCGCCG (SEQ ID NO: 5).

FIG. 1H illustrates variant genotyper module (168) for determining the variants at the Lynch I locus including an SNV with A/T alleles (169a) and the A monomer repeat (169b). FIG. 1H also illustrates variant analyzer modules (166) for curating sequence alignment data and providing them to the variant genotyper (168), and the implementations of the variant analyzer for the SNV with A/T alleles (167a) and the A monomer repeat (167b). The locus results from the genotyper are shown in FIG. 1H box 170, and specifically as the genotype of the SNV with A/T alleles (171a) and the A monomer repeat (171b).

In some implementations, the sequence graph includes two alternative paths for two alleles, and the method further involves genotyping the two or more alleles using sequence reads aligned to the two or more alternative paths. In some implementations, genotyping the two or more alleles involves providing coverages of the two or more alternative paths to a probabilistic model to determine the probabilities of the two or more alleles. In some implementations, the probabilistic model simulates a probability of an allele as a function of the coverage of the allele, the function being selected from a Poisson distribution, a negative-binomial distribution, a binomial distribution, or a beta-binomial distribution.

In some implementations, the probability function is a Poisson distribution, and its rate parameter is estimated from read length and mean depth observed at the genomic locus.

In the Poisson-based model, the probability of an allele is expressed as follows.

$$P(Y=y)=(C^y \times e^{-C})/y!$$

y is the read coverage of a base

C is the mean depth at the genomic locus

In some implementations, the mean depth C is estimated as.

$$C=LN/G$$

G is the length of the genomic locus

L is the read length

N is the number of all reads

GraphTools Library

In some implementations, the basic sequence graph functionality applies the GraphTools library. The library implements core graph abstractions (graphs themselves, graph paths, and graph alignments), operations on them, and algorithms for aligning linear sequences to graphs.

In some implementation, a sequence graph consists of nodes and directed edges. The graphs are allowed to contain self-loops (an edge connecting a node to itself) but no other cycles. The nodes contain sequences made up of core bases and IUPAC degenerate base codes.

A graph path is defined by a sequence of nodes that the path goes through together with the start position of the path on the first node and the end position on the last node. The positions are specified using the zero-based half-open coordinate system. The library defines multiple operations on paths including path extension and shrinkage, overlap checks, and path merging.

Graph alignments encode how linear query sequences (usually sequenced reads) are aligned to the graphs. In some implementations, a graph alignment comprises a graph path and a sequence of linear alignments defining the alignment of the query sequence to nodes of the graph path. Using the corresponding operations on paths, graph alignments can be shrunk or merged with other graph alignments. Path shrinking provides a mechanism for removing low confidence ends of the alignments while alignment merging is used by graph alignment algorithms for stitching together the full alignment of the query sequence from alignments of subsequences (e.g., kmers). In some implementations, the alignment algorithm operates by finding a kmer match between the query sequence and the graph and then extending this match to a full alignment. In some implementations, the alignment includes extracting a subgraph around the path corresponding to the kmer match (unrolling any loops in the process). Then it performs a Smith-Waterman alignment against the resulting directional acyclic graph. In some implementations, the algorithm supports affine gap penalties and is written using constant-length loops to enable compilers to generate SIMD code.

In some implementations, a graph path may be obtained with a search algorithm, which involves extending or shrinking a path by increasing or decreasing a number of repeats of a repeat unit represented by a self-loop until the alignment reaches a search criterion or convergence (e.g., an alignment score is maximized).

In some implementations, multiple graph paths are generated from a sequence graph, each graph path representing a specific number of repeats of a repeat unit represented by a self-loop. A query sequence is aligned to the multiple graph paths, and then the path meeting an alignment criterion is selected for the graph alignment.

Application Architecture

Some implementations are designed as a general tool for targeted variant genotyping (FIG. 1H). During each run, the program attempts to genotype a set of variants described in the variant catalog file. The variants located in close proximity of each other are grouped into the same locus. The locus structure is specified using a restricted subset of the regular expression (RE) syntax. REs contain sequences over the alphabet consisting of core base symbols and IUPAC degenerate base codes and must contain one or more of the expressions (<sequence>)?, (<sequence a>|<sequence b>), (<sequence>)*, (<sequence>)+ possibly separated by sequence interruptions. These expressions correspond to insertions/deletions, substitutions, sequence repeating 0 or more times, and sequence repeating at least once respectively. Additionally, the description of each locus contains a set of reference regions for that locus and reference coordinates of each constituent variant.

The bulk of the work is orchestrated by objects of LocusAnalyzer class that synthesizes a sequence graph representing the locus from the corresponding RE during initialization. After initialization, a locus analyzer processes the relevant reads by aligning them to the graph and then passing the resulting alignments to VariantAnalyzer that is defined for each variant contained in the locus. A VariantAnalyzer extracts information relevant for genotyping the associated variant and passes it to the Genotyper that performs the actual genotyping. The results output by each genotyper are then used to create the output VCF file.

For example, LocusAnalyzer responsible for processing the locus with pathogenic variant associated with Lynch I syndrome utilizes SNV analyzer and STR analyzer (FIG. 51, right panel).

Indel Genotyper

Some STRs may have a small insertion or deletion (indel) nearby. Such indels are modeled as additional sub-graphs in the flanking sequences of the STR. The number of reads mapped to each allele (or graph path) is modeled with a Poisson distribution whose rate parameter is estimated from the mean depth and read length observed at the locus. Genotype likelihoods are calculated under a Bayesian framework.

Identifying Repeat Expansions

Using the embodiments disclosed herein, one can determine various genetic conditions related to repeat expansion with high efficiency, sensitivity, and/or selectivity relative to conventional methods. Some embodiments of the invention provide methods for identifying and calling medically relevant repeat expansions such as the CGG repeat expansion that causes mental retardation in Fragile X syndrome using sequence reads that do not fully traverse the repeat sequence. Short reads such as 100 bp reads are not long enough to sequence through many repeat expansions. However, when analyzed with disclosed methods, samples with a repeat expansion show a statistically significant excess of reads containing a large number of the repeat sequence. Additionally, extremely large repeat expansions contain unaligned read pairs where both reads are entirely or almost entirely composed of the repeat sequence. Normal samples are used to identify the background expectations.

Conventional belief is that a repeat expansion cannot be detected without reads that span the entire repeat. Prior approaches to detecting repeat expansions use targeted sequencing with long reads and in some cases have been unsuccessful due to reads that are not long enough to span the repeat sequence. The results of some disclosed embodiments have been met with surprise partly because they use normal (non-targeted) sequence data and read length of only about 100 bp, but result in very high sensitivity for detecting repeat expansions. The methods set forth herein can detect the number of repeat units in a repeat expansion using paired reads having an insert length (i.e. two sequence reads and intervening sequence) that is shorter than the length of the entire repeat sequence.

Figure 2:
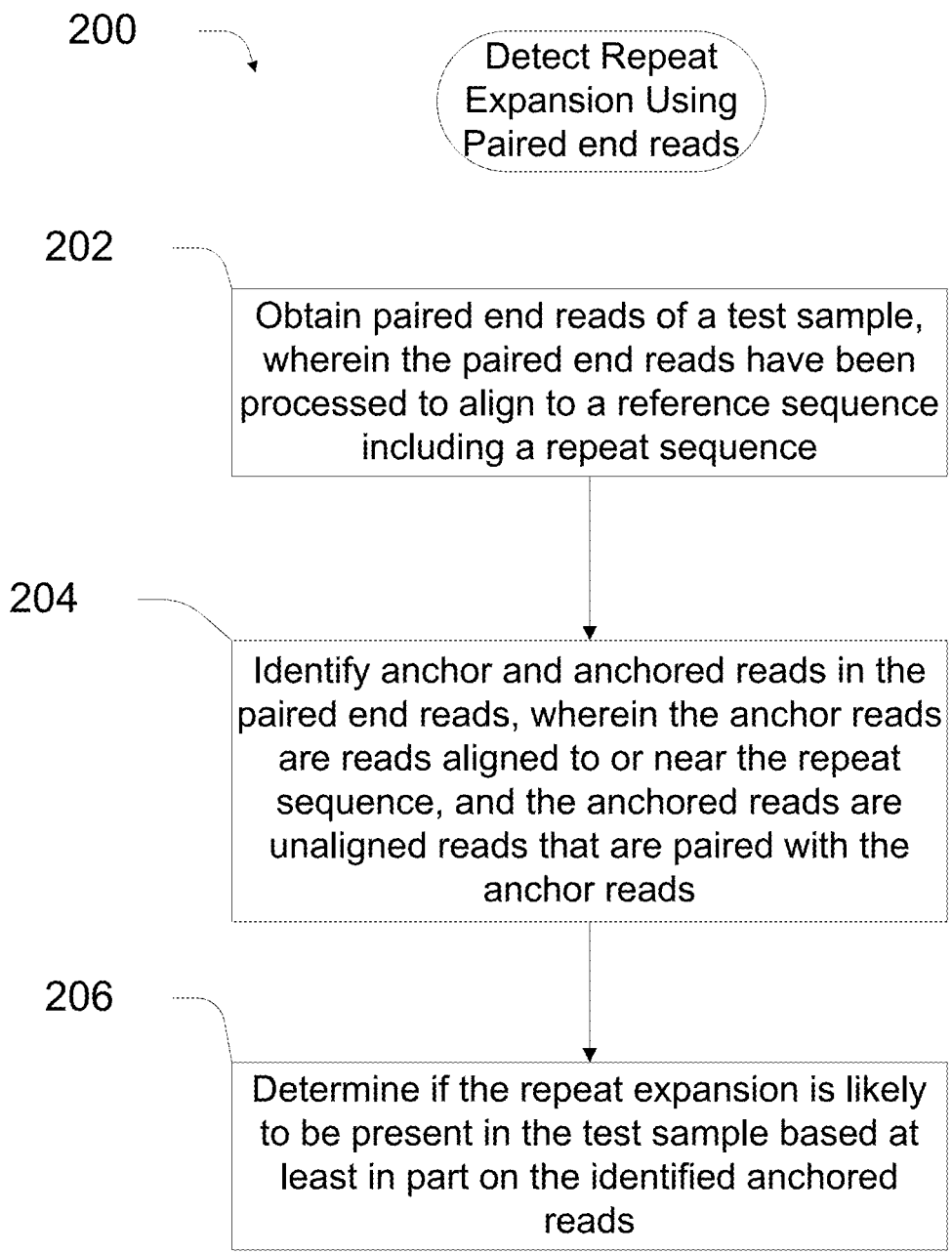
FIG. 2 is a flow diagram providing a high level depiction of an example of a method for determining the presence or absence of an expansion of a repeat sequence in a sample.

Turning to the details of methods for determining the presence of repeat expansion according to some embodiments, FIG. 2 shows a flow diagram providing a high level depiction of embodiments for determining the presence or absence of a repeat expansion of a repeat sequence in a sample. The repeat sequence is a nucleic acid sequence including the repetitive appearance of a short sequence referred to as a repeat unit. Table 1 above provides examples of repeat units, the numbers of repeats of the repeat units in the repeat sequences for normal and pathogenic sequences, the genes associated with the repeat sequences, and the diseases associated with the repeat expansion. Process 200 in FIG. 2 starts by obtaining paired end reads of a test sample. See block 202. The paired end reads have been processed to align to a reference sequence including a repeat sequence of interest. In some contexts, the alignment process is also referred to as a mapping process. The test sample includes nucleic acid and may be in the form of bodily fluids, tissues, etc., such as further described in the Sample Section below. The sequence reads have undergone an alignment process to be mapped to a reference sequence. Various alignment tools and algorithms may be used to attempt to align reads to the reference sequence as described elsewhere in the disclosure. As usual, in alignment algorithms, some reads are successfully aligned to the reference sequence, while others may not be successfully aligned or may be poorly aligned to the reference sequence. Reads that are successively aligned to the reference sequence are associated with sites on the reference sequence. Aligned reads and their associated sites are also referred to as sequence tags. As explained above, some sequence reads that contain a large number of repeats tend to be harder to align to the reference sequence. When a read is aligned to a reference sequence with a number of mismatched bases above a certain criterion, the read is considered poorly aligned. In various embodiments, reads are considered poorly aligned when they are aligned with at least about 1, 2, 3, 4, 5, 6, 7, 8, 9, or 10 mismatches. In other embodiments, reads are considered poorly aligned when they are aligned with at least about 5% of mismatches. In other embodiments, reads are considered poorly aligned when is they are aligned with at least about 10%, 15%, or 20% mismatched bases.

As illustrated in FIG. 2, process 200 proceeds to identify anchor reads and anchored reads in the paired end reads. See block 204. Anchor reads are reads among the paired end reads that are aligned to or near the repeat sequence of interest. For instance, an anchor read can align to a location on a reference sequence that is separated from a repeat sequence by a sequence length that is less than the sequence length of the insert. The separation length can be shorter. For example, the anchor read can align to a location on a reference sequence that is separated from a repeat sequence by a sequence length that is less than the sequence length of the anchor read or less than the combined sequence length of the anchor read and the sequence that connects the anchor read to the anchored read (i.e. the length of the insert minus the length of the anchored read). In some embodiments, the repeat sequence of interest may be the repeat sequence in the FMR1 gene including repeats of the repeat unit CGG. In a normal reference sequence, the repeat sequence in FMR1 gene includes about 6-32 repeats of the repeat unit CGG. As the repeats expand to over 200 copies, the repeat expansion tends to become pathogenic, causing Fragile X syndrome. In some embodiments, reads are considered aligned near the sequence of interest when it is aligned within 1000 bp of the repeat sequence of interest. In other embodiments, this parameter may be adjusted, such as within about 100 bp, 200 bp, 300 bp, 400 bp, 500 bp, 600 bp, 700 bp, 800 bp, 900 bp, 1500 bp, 2000 bp, 3000 bp, 5000 bp, etc. Additionally, the process also identifies anchored reads, which are reads that are paired to anchor reads, but are poorly aligned to or cannot be aligned to their reference sequence. Additional details of poorly aligned reads are described above.

Process 200 further involves determining if the repeat expansion of the repeat sequence is likely to be present in the test sample based at least in part on the identified anchored reads. See block 206. This determination step can involve various suitable analyses and computations as further described below. In some embodiments, the process uses the identified anchor reads, as well as the anchored reads, to determine if the repeat expansion is likely to be present. In some embodiments, the numbers of the repeats in the identified anchor and anchored reads are analyzed and compared to one or more criteria derived theoretically or derived from empirical data of an affected control samples.

In various embodiments described herein, repeats are obtained as in-frame repeats, where two repeats of the same repeat unit fall in the same reading frame. A reading frame is a way of dividing the sequence of nucleotides in a nucleic acid (DNA or RNA) molecule into a set of consecutive, non-overlapping triplets. During translation, triplets encode amino acids, and are termed codons. So any particular sequence has three possible reading frames. In some embodiments, repeats are counted according to three different reading frames, and the largest of the three counts is determined to be the number of corresponding repeats for the read.

Figure 3:
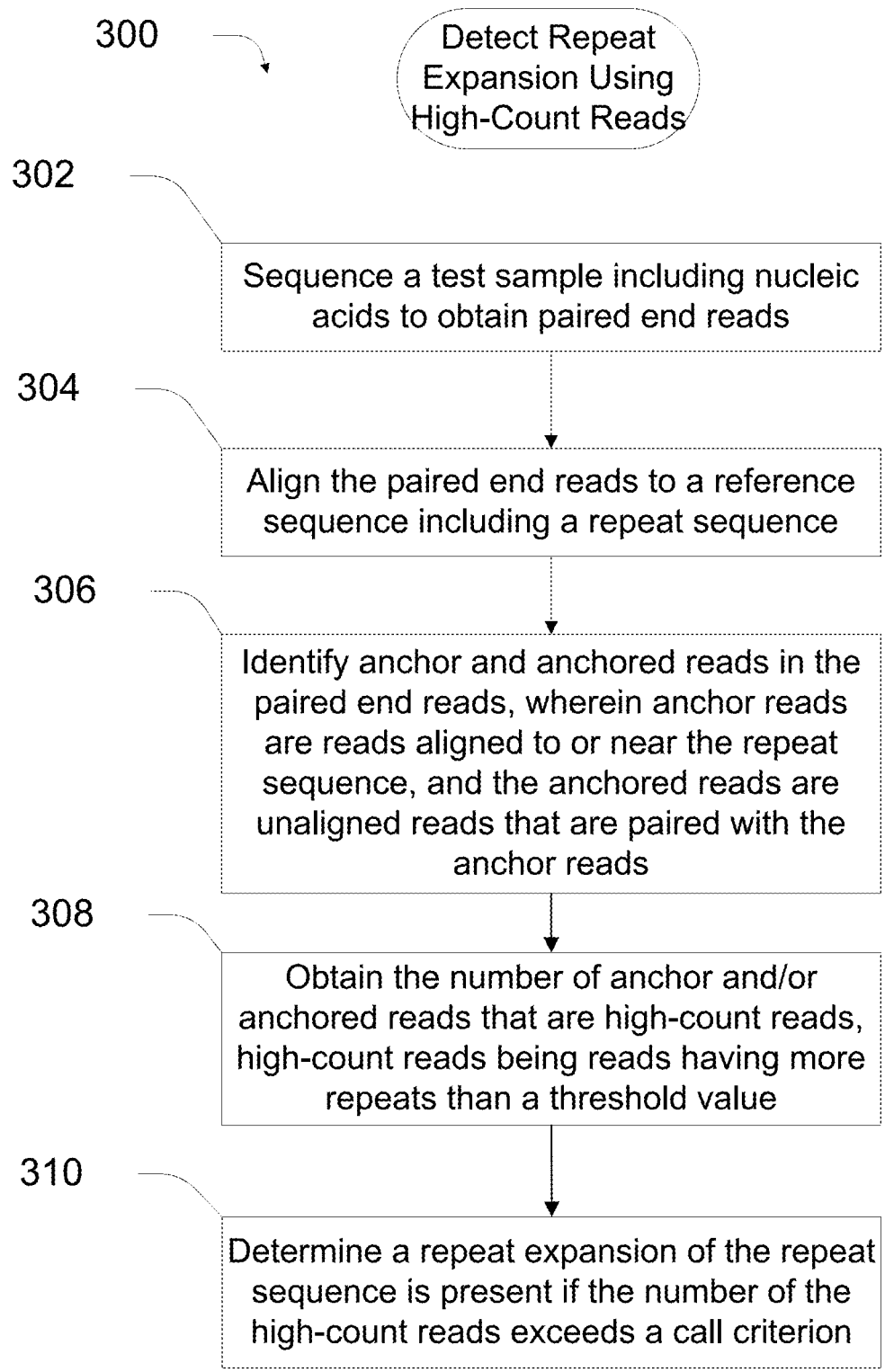
FIGS. 3 and 4 are flow diagrams illustrating examples of methods for detecting a repeat expansion using paired end reads.

An example of a process involving additional operation and analyses is illustrated in FIG. 3. FIG. 3 shows a flow diagram illustrating a process 300 for detecting repeat expansion using paired end reads having a large number of repeats. Process 300 includes additional upstream acts for processing the test sample. The process starts by sequencing a test sample including nucleic acids to obtain paired end reads. See block 302. In some embodiments, the test sample may be obtained and prepared in various ways as further described in the Samples Section below. For instance, the test sample may be a biological fluid, e.g., plasma, or any suitable sample as described below. The sample may be obtained using a non-invasive procedure such as a simple blood draw. In some embodiments, a test sample contains a mixture of nucleic acid molecules, e.g., cfDNA molecules. In some embodiments, the test sample is a maternal plasma sample that contains a mixture of fetal and maternal cfDNA molecules.

Before sequencing, nucleic acids are extracted from the sample. Suitable extraction processes and apparatus are described elsewhere herein. In some implementations, the apparatus processes DNA from multiple samples together to provide multiplexed libraries and sequence data. In some embodiments, the apparatus processes DNA from eight or more test samples in parallel. As described below, a sequencing system may process extracted DNA to produce a library of coded (e.g., bar coded) DNA fragments.

In some embodiments, the nucleic acids in the test sample may be further processed to prepare sequencing libraries for multiplex or singleplex sequencing, as further described in the Sequencing Library Preparation Section below. After the samples are processed and prepared, sequencing of the nucleic acid may be performed by various methods. In some embodiments, various next generation sequencing platforms and protocols may be employed, which are further described in the Sequencing Methods Section below.

Regardless of the specific sequencing platform and protocol, in block 302, at least a portion of the nucleic acids contained in the sample are sequenced to generate tens of thousands, hundreds of thousands, or millions of sequence reads, e.g., 100 bp reads. In some embodiments, the reads include paired end reads. In other embodiments, such as those described below with reference to FIG. 5, in addition to paired end reads, single-end long reads including over hundreds, thousands, or tens of thousands bases may be used to determine a repeat sequence. In some embodiments, the sequence reads comprise about 20 bp, about 25 bp, about 30 bp, about 35 bp, about 36 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. It is expected that technological advances will enable single-end reads of greater than 500 bp and enabling for reads of greater than about 1000 bp when paired end reads are generated.

Process 300 proceeds to align the paired end reads obtained from block 302 to a reference sequence including a repeat sequence. See block 304. In some embodiments, the repeat sequence is prone to expansion. In some embodiments the repeat expansion is known to be associated with a genetic disorder. In other embodiments, the repeat expansion of the repeat sequence has not been a previously studied to establish an association with a genetic disorder. The methods disclosed herein allow detection of a repeat sequence and repeat expansion regardless of any associated pathology. In some embodiments, reads are aligned to a reference genome, e.g., hg18. In other embodiments, reads are aligned to a portion of a reference genome, e.g., a chromosome or a chromosome segment. The reads that are uniquely mapped to the reference genome are known as sequence tags. In one embodiment, at least about $3 \times 10^6$ qualified sequence tags, at least about $5 \times 10^6$ qualified sequence tags, at least about $8 \times 10^6$ qualified sequence tags, at least about $10 \times 10^6$ qualified sequence tags, at least about $15 \times 10^6$ qualified sequence tags, at least about $20 \times 10^6$ qualified sequence tags, at least about $30 \times 10^6$ qualified sequence tags, at least about $40 \times 10^6$ qualified sequence tags, or at least about $50 \times 10^6$ qualified sequence tags are obtained from reads that map uniquely to a reference genome.

In some embodiments, the process may filter sequence reads prior to alignment. In some embodiments, read filtering is a quality-filtering process enabled by software programs implemented in the sequencer to filter out erroneous and low quality reads. For example, Illumina's Sequencing Control Software (SCS) and Consensus Assessment of Sequence and Variation software programs filter out erroneous and low quality reads by converting raw image data generated by the sequencing reactions into intensity scores, base calls, quality scored alignments, and additional formats to provide biologically relevant information for downstream analysis.

In certain embodiments, the reads produced by sequencing apparatus are provided in an electronic format. Alignment is accomplished using computational apparatus as discussed below. Individual reads are compared against the reference genome, which is often vast (millions of base pairs) to identify sites where the reads uniquely correspond with the reference genome. In some embodiments, the alignment procedure permits limited mismatch between reads and the reference genome. In some cases, 1, 2, 3, or more base pairs in a read are permitted to mismatch corresponding base pairs in a reference genome, and yet a mapping is still made. In some embodiments, reads are considered aligned reads when the reads are aligned to the reference sequence with no more than 1, 2, 3, or 4 base pairs. Correspondingly, unaligned reads are reads that cannot be aligned or are poorly aligned. Poorly aligned reads are reads having more mismatches than aligned reads. In some embodiments, reads are considered aligned reads when the reads are aligned to the reference sequence with no more than 1%, 2%, 3%, 4%, 5%, or 10% of base pairs.

After aligning the paired end reads to the reference sequence including the repeat sequence of interest, process 300 proceeds to identify anchor reads and anchored reads among the paired end reads. See block 306. As mentioned above, anchor reads are paired end reads aligned to or near the repeat sequence. In some embodiments anchor reads are paired end reads that are aligned within 1 kb of the repeat sequence. Anchored reads are paired with anchor reads, but they cannot be or are poorly aligned to the reference sequence as explained above.

Process 300 analyzes the numbers of repeats of repeat units in the identified anchor and/or anchored reads to determine the presence or absence of an expansion of the repeat sequence. More specifically, process 300 involves using the numbers of repeats in reads to obtain numbers of high-count reads in anchor and/or anchored reads. High-count reads are reads having more repeats than a threshold value. In some embodiments, the high-count reads are obtained only from the anchored reads. In other embodiments, the high-count reads are obtained from both the anchor and anchored reads. In some embodiments, if the number of repeats is close to the maximum number of repeats possible for a read, the read is considered a high-count read. For instance, if a read is 100 bp, and a repeat unit under consideration is 3 bp, the maximum number of repeats would be 33. In other words, the maximum is calculated from the length of the paired end reads and the length of the repeat unit. Specifically, the maximum number of repeats may be obtained by dividing the read length by the length of the repeat unit and rounding down the number. In this example, various implementations may identify 100 bp reads having at least about 28, 29, 30, 31, 32, or 33 repeats as high-count reads. The number of repeats may be adjusted upward or downward for high-count reads based on empirical factors and considerations. In various embodiments, the threshold value for high-count reads is at least about 80%, 85%, 90%, or 95% of the maximum number of repeats.

Process 300 then determines if a repeat expansion of the repeat sequence is likely present based on the number of high-count reads. See block 310. In some embodiments, the analysis compares the obtained high-count reads to a call criterion, and determines that the repeat expansion is likely present if the criterion is exceeded. In some embodiments, the call criterion is obtained from a distribution of high-count reads of control samples. For instance, a plurality of control samples known to have or suspected of having a normal repeat sequence are analyzed, and high-count reads are obtained for the control samples in the same way as described above. The distribution of high count reads for the control samples can be obtained, and the probability of an unaffected sample having high count reads more than a particular value can be estimated. This probability allows determination of sensitivity and selectivity given a call criterion set at this particular value. In some embodiments, the call criterion is set at a threshold value such that the probability of an unaffected sample having high-count reads more than the threshold value is less than 5%. In other words, the p-value is smaller than 0.05. In these embodiments, as the repeats expand, the repeat sequence gets longer, more reads are possible to originate from completely within the repeat sequence, and more high-count reads can be obtained for a sample. In various alternative implementations, a more conservative call criterion may be chosen such that the probability of an unaffected sample having more high-count reads than the threshold value is less than about 1%, 0.1%, 0.01%, 0.001%, 0.0001%, etc. It will be appreciated that the call criterion can be adjusted upward or downward based on the various factors and the need to increase sensitivity or selectivity of the test.

In some embodiments, instead of or in addition to empirically obtaining a call criterion of the number of high-count reads from control samples, a call criterion may be obtained theoretically for determining a repeat expansion. It is possible to calculate the expected number of reads that are fully within a repeat given a number of parameters including the length of the paired end reads, the length of a sequence having the repeat expansion, and a sequencing depth. For instance, one can use a sequencing depth to calculate the average spacing between reads in the aligned genome. If one has sequenced an individual sample to 30× depth, the total bases sequenced are equal to the size of the genome multiplied by the depth. For humans this would amount to about $3 \times 10^9 \times 30 = 9 \times 10^{10}$. If each read is 100 bp long, then there are a total of $9 \times 10^8$ reads required to achieve this depth. Since a genome is diploid, half of these reads are sequencing one chromosome/haplotype, and the rest are sequencing the other chromosome/haplotype. Per haplotype there are $4.5 \times 10^8$ reads and dividing the total genome size by this number yields the average spacing between starting positions of each read—i.e. $3 \times 10^9 / 4.5 \times 10^8 = 1$ read every 6.7 bp on average. One can use this number to estimate the number of reads that will be fully within a repeat sequence based on the size of that repeat sequence in a particular individual. If the total repeat sequence size is 300 bp then any read that starts within the first 200 bp of that repeat sequence will be fully within the repeat sequence (any read that starts within the last 100 bp will be, at least, partially outside of the repeat sequence based on 100 bp read lengths). Since it is expected that a read will align every 6.7 bp, one expects 200 bp/(6.7 bp/read)=30 reads to fully align within the repeat sequence. Though there will be variability around this number, this allows one to estimate the total reads that will be fully within the repeat sequence for any expansion size. Repeat sequence lengths and corresponding expected numbers of reads fully aligned in the repeat sequence calculated according to this method are given in Table 2 of Example 1 below.

In some embodiments, a call criterion is calculated from the distance between the first and last observation of the repeat sequence within the reads, thus allowing for mutations in the repeat sequence and sequencing errors.

In some embodiments, the process may further include diagnosing that the individual from whom the test sample is obtained with an elevated risk of a genetic disorder such as Fragile X syndrome, ALS, Huntington's disease, Friedreich's ataxia, spinocerebellar ataxia, spino-bulbar muscular atrophy, myotonic dystrophy, Machado-Joseph disease, dentatorubral pallidoluysian atrophy, etc. Such a diagnosis may be based on a determination that the repeat expansion is likely present in the test sample, and on the gene and repeat sequence associated with the repeat expansion. In other embodiments, when a genetic disorder is not known, some embodiments may detect abnormally high counts of repeats to newly identify genetic causes of a disease.

Figure 4:
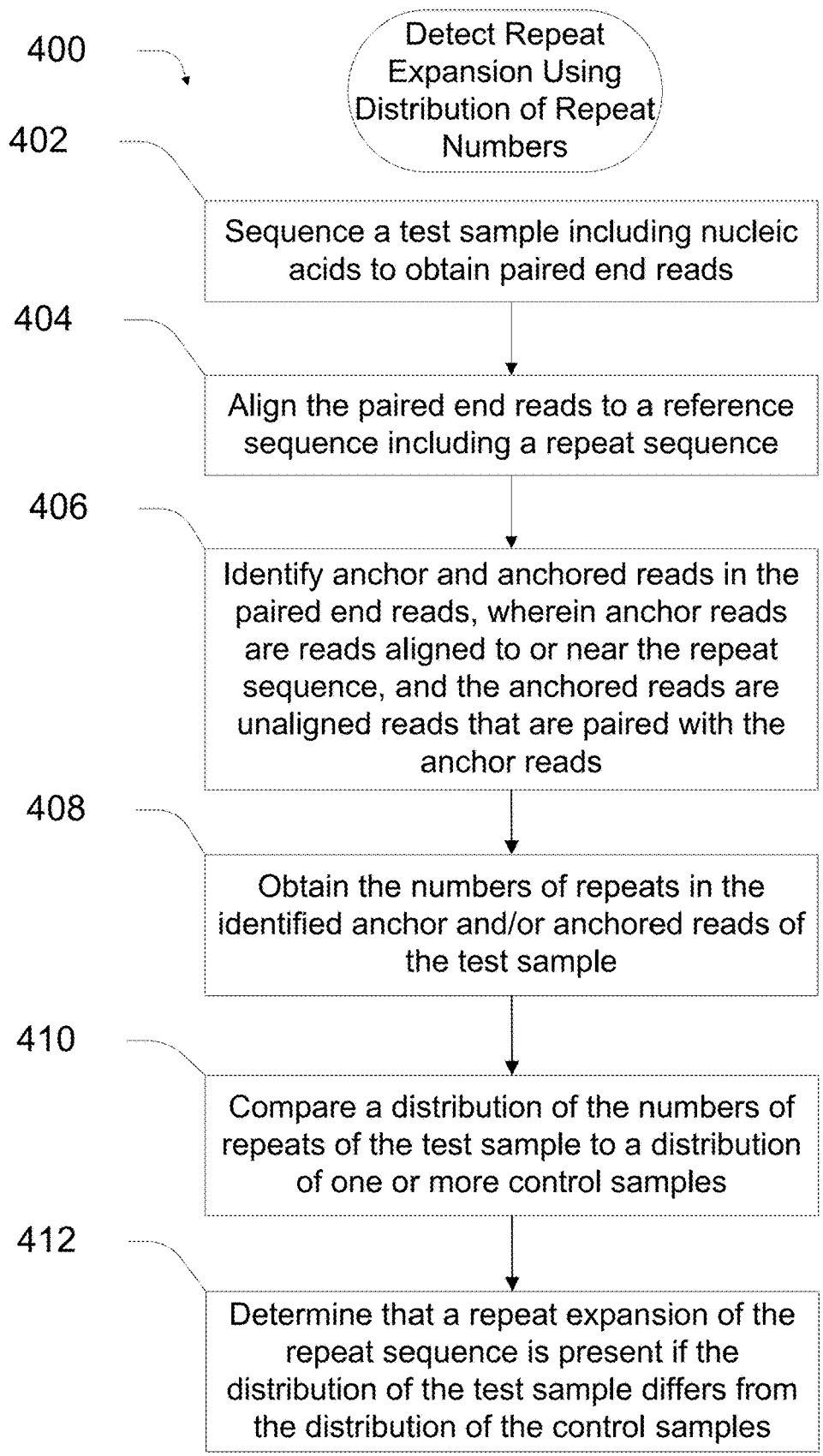

FIG. 4 is a flowchart illustrating another process for detecting repeat expansion according to some embodiments. Process 400 uses the numbers of repeats in the paired end reads of the test sample instead of high-count reads to determine the presence of the repeat expansion. Process 400 starts by sequencing a test sample including nucleic acid to obtain paired end reads. See block 402, which is equivalent to block 302 of process 300. Process 400 continues by aligning the paired end reads to a reference sequence including the repeat sequence. See block 404, which is equivalent to block 304 in process 300. The process proceeds by identifying anchor and anchor reads in the paired end reads, with anchor reads being reads aligned to or near the repeat sequence, and the anchored reads being unaligned reads that are paired with the anchor reads. In some embodiments, unaligned reads include both reads that cannot be aligned to and reads that are poorly aligned to the reference sequence.

After identifying the anchor and anchored reads, process 400 obtains the numbers of repeats in the anchor and/or anchored reads from the test sample. See block 408. The process then obtains a distribution of the numbers of repeats for all the anchor and/or anchored reads obtained from the test sample. In some embodiments, only the numbers of repeats from anchored reads are analyzed. In other embodiments, repeats of both anchored reads and anchor reads are analyzed. Then the distribution of the numbers of repeats of the test sample is compared to a distribution of one or more control samples. See block 410. In some embodiments, the process determines that repeat expansion of the repeat sequence is present in the test sample if the distribution of the test sample statistically significantly differs from the distribution of the control samples. See the block 412. Process 400 analyzes numbers of repeats for reads including high-count as well as low-count reads, which is different from a process that analyzes only high-count reads, such as described above with respect to process 300.

In some embodiments, comparison of the test sample's distribution and the control samples' distribution involves using a Mann-Whitney rank test to determine if the two distributions are significantly different. In some embodiments, the analysis determines that the repeat expansion is likely present in the test sample if the test sample's distribution is skewed more towards higher numbers of repeats relative to the control samples, and the p-value for the Mann-Whitney rank test is smaller than about 0.0001 or 0.00001. The p-value may be adjusted as necessary to improve selectivity or sensitivity of the test.

The processes for detecting repeat expansion described above with respect to FIGS. 2-4 use anchored reads, which are unaligned reads that are paired to reads aligned to a repeat sequence of interest. Variations on these processes could include searching through the unaligned reads for read pairs that are both almost entirely composed of some type of repeat sequence to discover new, previously unidentified repeat expansions that may be medically relevant. This method does not quantify the exact number of repeats but is powerful to identify extreme repeat expansions or outliers that should be flagged for further quantification. Combined with longer reads this method may be able to both identify and quantify repeats of up to 200 bp or more in total length.

Figure 5:
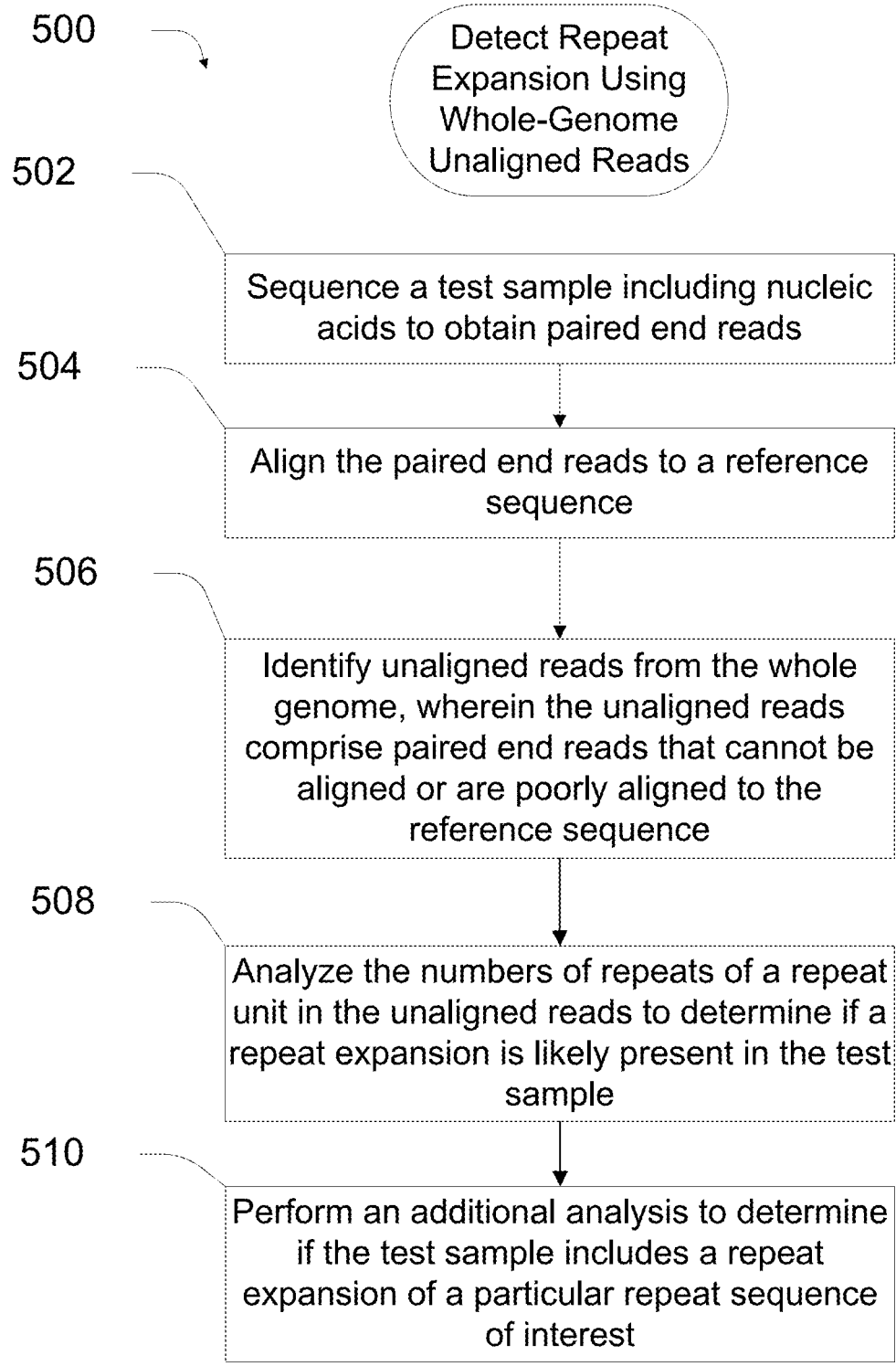
FIG. 5 is a flow diagram of a method that uses unaligned reads not associated with any repeat sequence of interest to determine a repeat expansion.

FIG. 5 illustrates a flow diagram of a process 500 that uses unaligned reads not associated with any repeat sequence of interest to identify a repeat expansion. Process 500 may use whole genome unaligned reads to detect repeat expansion. The process starts by sequencing a test sample including nucleic acids to obtain paired end reads. See block 502. Process 500 proceeds by aligning the paired end reads to a reference genome. See block 504. The process then identifies unaligned reads for the whole genome. The unaligned reads include paired end reads that cannot be aligned or are poorly aligned to the reference sequence. See block 506. The process then analyzes the numbers of repeats of a repeat unit in the unaligned reads to determine if a repeat expansion is likely present in the test sample. This analysis can be agnostic of any particular repeat sequence. The analysis can be applied to various potential repeat units, and the numbers of repeats for different repeat units from a test sample can be compared to those of a plurality of control samples. Comparison techniques between a test sample and control samples described above may be applied in this analysis. If the comparison shows that a test sample has an abnormally high number of repeats of a repeat unit, an additional analysis may be performed to determine if the test sample includes the repeat expansion of the particular repeat sequence of interest. See block 510.

In some embodiments, the additional analysis involves very long sequence reads that potentially can span long repeat sequences having repeat expansions that are medically relevant. The reads in this additional analysis are longer than the paired end reads. In some embodiments, single molecule sequencing or synthetic long-read sequencing are used to obtain long reads. In some embodiments, the relation between the repeat expansion and a genetic disorder is known in the art. In other embodiments, however, the relation between the repeat expansion and a genetic disorder does not need to be established in the art.

In some embodiments, analyzing the numbers of repeats of the repeat unit in the unaligned reads of operation 510 involves a high-count analysis comparable to that of operation 308 of FIG. 3. The analysis includes obtaining the number of high-count reads, wherein the high-count reads are unaligned reads having more repeats than a threshold value; and comparing the number of high-count reads in the test sample to a call criterion. In some embodiments, the threshold value for high-count reads is at least about 80% of the maximum number of repeats, which maximum is calculated as the ratio of the length of the paired end reads over the length of the repeat unit. In some embodiments, the high-count reads also include reads that are paired to the unaligned reads and have more repeats than the threshold value.

In some embodiments, prior to the additional analysis of operation 510, the process further involves (a) identifying paired end reads that are paired to the unaligned reads and are aligned to or near a repeat sequence on the reference genome; and (b) providing the repeat sequence as the particular repeat sequence of interest for operation 510. Then the additional analysis of the repeat sequence of interest may employ any of the methods described above in association with FIGS. 2-4.

Samples

Samples that are used for determining repeat expansion can include samples taken from any cell, fluid, tissue, or organ including nucleic acids in which repeat expansion for one or more repeat sequences of interest are to be determined. In some embodiments involving diagnosis of fetus, it is advantageous to obtain cell-free nucleic acids, e.g., cell-free DNA (cfDNA), from maternal body fluid. Cell-free nucleic acids, including cell-free DNA, can be obtained by various methods known in the art from biological samples including but not limited to plasma, serum, and urine (see, e.g., Fan et al., Proc Natl Acad Sci 105:16266-16271 [2008]; Koide et al., Prenatal Diagnosis 25:604-607 [2005]; Chen et al., Nature Med. 2: 1033-1035 [1996]; Lo et al., Lancet 350: 485-487 [1997]; Botezatu et al., Clin Chem. 46: 1078-1084, 2000; and Su et al., J Mol. Diagn. 6: 101-107 [2004]).

In various embodiments the nucleic acids (e.g., DNA or RNA) present in the sample can be enriched specifically or non-specifically prior to use (e.g., prior to preparing a sequencing library). DNA are used as an example of nucleic acids in the illustrative examples below. Non-specific enrichment of sample DNA refers to the whole genome amplification of the genomic DNA fragments of the sample that can be used to increase the level of the sample DNA prior to preparing a cfDNA sequencing library. Methods for whole genome amplification are known in the art. Degenerate oligonucleotide-primed PCR (DOP), primer extension PCR technique (PEP) and multiple displacement amplification (MDA) are examples of whole genome amplification methods. In some embodiments, the sample is un-enriched for DNA.

The sample including the nucleic acids to which the methods described herein are applied typically include a biological sample ("test sample") as described above. In some embodiments, the nucleic acids to be screened for repeat expansion are purified or isolated by any of a number of well-known methods.

Accordingly, in certain embodiments the sample includes or consists essentially of a purified or isolated polynucleotide, or it can include samples such as a tissue sample, a biological fluid sample, a cell sample, and the like. Suitable biological fluid samples include, but are not limited to blood, plasma, serum, sweat, tears, sputum, urine, sputum, ear flow, lymph, saliva, cerebrospinal fluid, ravages, bone marrow suspension, vaginal flow, trans-cervical lavage, brain fluid, ascites, milk, secretions of the respiratory, intestinal and genitourinary tracts, amniotic fluid, milk, and leukophoresis samples. In some embodiments, the sample is a sample that is easily obtainable by non-invasive procedures, e.g., blood, plasma, serum, sweat, tears, sputum, urine, sputum, ear flow, saliva or feces. In certain embodiments the sample is a peripheral blood sample, or the plasma and/or serum fractions of a peripheral blood sample. In other embodiments, the biological sample is a swab or smear, a biopsy specimen, or a cell culture. In another embodiment, the sample is a mixture of two or more biological samples, e.g., a biological sample can include two or more of a biological fluid sample, a tissue sample, and a cell culture sample. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

In certain embodiments, samples can be obtained from sources, including, but not limited to, samples from different individuals, samples from different developmental stages of the same or different individuals, samples from different diseased individuals (e.g., individuals suspected of having a genetic disorder), normal individuals, samples obtained at different stages of a disease in an individual, samples obtained from an individual subjected to different treatments for a disease, samples from individuals subjected to different environmental factors, samples from individuals with predisposition to a pathology, samples individuals with exposure to an infectious disease agent, and the like.

In one illustrative, but non-limiting embodiment, the sample is a maternal sample that is obtained from a pregnant female, for example a pregnant woman. In this instance, the sample can be analyzed using the methods described herein to provide a prenatal diagnosis of potential chromosomal abnormalities in the fetus. The maternal sample can be a tissue sample, a biological fluid sample, or a cell sample. A biological fluid includes, as non-limiting examples, blood, plasma, serum, sweat, tears, sputum, urine, sputum, ear flow, lymph, saliva, cerebrospinal fluid, ravages, bone marrow suspension, vaginal flow, transcervical lavage, brain fluid, ascites, milk, secretions of the respiratory, intestinal and genitourinary tracts, and leukophoresis samples.

In certain embodiments samples can also be obtained from in vitro cultured tissues, cells, or other polynucleotide-containing sources. The cultured samples can be taken from sources including, but not limited to, cultures (e.g., tissue or cells) maintained in different media and conditions (e.g., pH, pressure, or temperature), cultures (e.g., tissue or cells) maintained for different periods of length, cultures (e.g., tissue or cells) treated with different factors or reagents (e.g., a drug candidate, or a modulator), or cultures of different types of tissue and/or cells.

Methods of isolating nucleic acids from biological sources are well known and will differ depending upon the nature of the source. One of skill in the art can readily isolate nucleic acids from a source as needed for the method described herein. In some instances, it can be advantageous to fragment the nucleic acid molecules in the nucleic acid sample. Fragmentation can be random, or it can be specific, as achieved, for example, using restriction endonuclease digestion. Methods for random fragmentation are well known in the art, and include, for example, limited DNAse digestion, alkali treatment and physical shearing.

Sequencing Library Preparation

In various embodiments, sequencing may be performed on various sequencing platforms that require preparation of a sequencing library. The preparation typically involves fragmenting the DNA (sonication, nebulization or shearing), followed by DNA repair and end polishing (blunt end or A overhang), and platform-specific adaptor ligation. In one embodiment, the methods described herein can utilize next generation sequencing technologies (NGS), that allow multiple samples to be sequenced individually as genomic molecules (i.e., singleplex sequencing) or as pooled samples comprising indexed genomic molecules (e.g., multiplex sequencing) on a single sequencing run. These methods can generate up to several hundred million reads of DNA sequences. In various embodiments the sequences of genomic nucleic acids, and/or of indexed genomic nucleic acids can be determined using, for example, the Next Generation Sequencing Technologies (NGS) described herein. In various embodiments analysis of the massive amount of sequence data obtained using NGS can be performed using one or more processors as described herein.

In various embodiments the use of such sequencing technologies does not involve the preparation of sequencing libraries.

However, in certain embodiments the sequencing methods contemplated herein involve the preparation of sequencing libraries. In one illustrative approach, sequencing library preparation involves the production of a random collection of adapter-modified DNA fragments (e.g., polynucleotides) that are ready to be sequenced. Sequencing libraries of polynucleotides can be prepared from DNA or RNA, including equivalents, analogs of either DNA or cDNA, for example, DNA or cDNA that is complementary or copy DNA produced from an RNA template, by the action of reverse transcriptase. The polynucleotides may originate in double-stranded form (e.g., dsDNA such as genomic DNA fragments, cDNA, PCR amplification products, and the like) or, in certain embodiments, the polynucleotides may originated in single-stranded form (e.g., ssDNA, RNA, etc.) and have been converted to dsDNA form. By way of illustration, in certain embodiments, single stranded mRNA molecules may be copied into double-stranded cDNAs suitable for use in preparing a sequencing library. The precise sequence of the primary polynucleotide molecules is generally not material to the method of library preparation, and may be known or unknown. In one embodiment, the polynucleotide molecules are DNA molecules. More particularly, in certain embodiments, the polynucleotide molecules represent the entire genetic complement of an organism or substantially the entire genetic complement of an organism, and are genomic DNA molecules (e.g., cellular DNA, cell free DNA (cfDNA), etc.), that typically include both intron sequence and exon sequence (coding sequence), as well as non-coding regulatory sequences such as promoter and enhancer sequences. In certain embodiments, the primary polynucleotide molecules comprise human genomic DNA molecules, e.g., cfDNA molecules present in peripheral blood of a pregnant subject.

Preparation of sequencing libraries for some NGS sequencing platforms is facilitated by the use of polynucleotides comprising a specific range of fragment sizes. Preparation of such libraries typically involves the fragmentation of large polynucleotides (e.g. cellular genomic DNA) to obtain polynucleotides in the desired size range.

Paired end reads are used for the methods and systems disclosed herein for determining repeat expansion. The fragment or insert length is longer than the read length, and typically longer than the sum of the lengths of the two reads.

In some illustrative embodiments, the sample nucleic acid(s) are obtained as genomic DNA, which is subjected to fragmentation into fragments of approximately 100 or more, approximately 200 or more, approximately 300 or more, approximately 400 or more, or approximately 500 or more base pairs, and to which NGS methods can be readily applied. In some embodiments, the paired end reads are obtained from inserts of about 100-5000 bp. In some embodiments, the inserts are about 100-1000 bp long. These are sometimes implemented as regular short-insert paired end reads. In some embodiments, the inserts are about 1000-5000 bp long. These are sometimes implemented as long-insert mate paired reads as described above.

In some implementations, long inserts are designed for evaluating very long, expanded repeat sequences. In some implementations, mate pair reads may be applied to obtain reads that are spaced apart by thousands of base pairs. In these implementations, inserts or fragments range from hundreds to thousands of base pairs, with two biotin junction adaptors on the two ends of an insert. Then the biotin junction adaptors join the two ends of the insert to form a circularized molecule, which is then further fragmented. A sub-fragment including the biotin junction adaptors and the two ends of the original insert is selected for sequencing on a platform that is designed to sequence shorter fragments.

Fragmentation can be achieved by any of a number of methods known to those of skill in the art. For example, fragmentation can be achieved by mechanical means including, but not limited to nebulization, sonication and hydroshear. However mechanical fragmentation typically cleaves the DNA backbone at C—O, P—O and C—C bonds resulting in a heterogeneous mix of blunt and 3'- and 5'-overhanging ends with broken C—O, P—O and/C—C bonds (see, e.g., Alnemri and Liwack, J Biol. Chem 265:17323-17333 [1990]; Richards and Boyer, J Mol Biol 11:327-240 [1965]) which may need to be repaired as they may lack the requisite 5'-phosphate for the subsequent enzymatic reactions, e.g., ligation of sequencing adaptors, that are required for preparing DNA for sequencing.

In contrast, cfDNA, typically exists as fragments of less than about 300 base pairs and consequently, fragmentation is not typically necessary for generating a sequencing library using cfDNA samples.

Typically, whether polynucleotides are forcibly fragmented (e.g., fragmented in vitro), or naturally exist as fragments, they are converted to blunt-ended DNA having 5'-phosphates and 3'-hydroxyl. Standard protocols, e.g., protocols for sequencing using, for example, the Illumina platform as described elsewhere herein, instruct users to end-repair sample DNA, to purify the end-repaired products prior to dA-tailing, and to purify the dA-tailing products prior to the adaptor-ligating steps of the library preparation.

Various embodiments of methods of sequence library preparation described herein obviate the need to perform one or more of the steps typically mandated by standard protocols to obtain a modified DNA product that can be sequenced by NGS. An abbreviated method (ABB method), a 1-step method, and a 2-step method are examples of methods for preparation of a sequencing library, which can be found in patent application Ser. No. 13/555,037 filed on Jul. 20, 2012, which is incorporated by reference by its entirety.

Sequencing Methods

As indicated above, the prepared samples (e.g., Sequencing Libraries) are sequenced as part of the procedure for identifying copy number variation(s). Any of a number of sequencing technologies can be utilized.

Some sequencing technologies are available commercially, such as the sequencing-by-hybridization platform from Affymetrix Inc. (Sunnyvale, CA) and the sequencing-by-synthesis platforms from 454 Life Sciences (Bradford, CT), Illumina/Solexa (San Diego, CA) and Helicos Biosciences (Cambridge, MA), and the sequencing-by-ligation platform from Applied Biosystems (Foster City, CA), as described below. In addition to the single molecule sequencing performed using sequencing-by-synthesis of Helicos Biosciences, other single molecule sequencing technologies include, but are not limited to, the SMRT™ technology of Pacific Biosciences, the ION TORRENT™ technology, and nanopore sequencing developed for example, by Oxford Nanopore Technologies.

While the automated Sanger method is considered as a 'first generation' technology, Sanger sequencing including the automated Sanger sequencing, can also be employed in the methods described herein. Additional suitable sequencing methods include, but are not limited to nucleic acid imaging technologies, e.g., atomic force microscopy (AFM) or transmission electron microscopy (TEM). Illustrative sequencing technologies are described in greater detail below.

In some embodiments, the disclosed methods involve obtaining sequence information for the nucleic acids in the test sample by massively parallel sequencing of millions of DNA fragments using Illumina's sequencing-by-synthesis and reversible terminator-based sequencing chemistry (e.g. as described in Bentley et al., Nature 6:53-59 [2009]). Template DNA can be genomic DNA, e.g., cellular DNA or cfDNA. In some embodiments, genomic DNA from isolated cells is used as the template, and it is fragmented into lengths of several hundred base pairs. In other embodiments, cfDNA is used as the template, and fragmentation is not required as cfDNA exists as short fragments. For example fetal cfDNA circulates in the bloodstream as fragments approximately 170 base pairs (bp) in length (Fan et al., Clin Chem 56:1279-1286 [2010]), and no fragmentation of the DNA is required prior to sequencing. Illumina's sequencing technology relies on the attachment of fragmented genomic DNA to a planar, optically transparent surface on which oligonucleotide anchors are bound. Template DNA is end-repaired to generate 5'-phosphorylated blunt ends, and the polymerase activity of Klenow fragment is used to add a single A base to the 3' end of the blunt phosphorylated DNA fragments. This addition prepares the DNA fragments for ligation to oligonucleotide adapters, which have an overhang of a single T base at their 3' end to increase ligation efficiency. The adapter oligonucleotides are complementary to the flow-cell anchor oligos (not to be confused with the anchor/anchored reads in the analysis of repeat expansion). Under limiting-dilution conditions, adapter-modified, single-stranded template DNA is added to the flow cell and immobilized by hybridization to the anchor oligos. Attached DNA fragments are extended and bridge amplified to create an ultra-high density sequencing flow cell with hundreds of millions of clusters, each containing about 1,000 copies of the same template. In one embodiment, the randomly fragmented genomic DNA is amplified using PCR before it is subjected to cluster amplification. Alternatively, an amplification-free genomic library preparation is used, and the randomly fragmented genomic DNA is enriched using the cluster amplification alone (Kozarewa et al., Nature Methods 6:291-295 [2009]). The templates are sequenced using a robust four-color DNA sequencing-by-synthesis technology that employs reversible terminators with removable fluorescent dyes. High-sensitivity fluorescence detection is achieved using laser excitation and total internal reflection optics. Short sequence reads of about tens to a few hundred base pairs are aligned against a reference genome and unique mapping of the short sequence reads to the reference genome are identified using specially developed data analysis pipeline software. After completion of the first read, the templates can be regenerated in situ to enable a second read from the opposite end of the fragments. Thus, either single-end or paired end sequencing of the DNA fragments can be used.

Various embodiments of the disclosure may use sequencing by synthesis that allows paired end sequencing. In some embodiments, the sequencing by synthesis platform by Illumina involves clustering fragments. Clustering is a process in which each fragment molecule is isothermally amplified. In some embodiments, as the example described here, the fragment has two different adaptors attached to the two ends of the fragment, the adaptors allowing the fragment to hybridize with the two different oligos on the surface of a flow cell lane. The fragment further includes or is connected to two index sequences at two ends of the fragment, which index sequences provide labels to identify different samples in multiplex sequencing. In some sequencing platforms, a fragment to be sequenced is also referred to as an insert.

In some implementation, a flow cell for clustering in the Illumina platform is a glass slide with lanes. Each lane is a glass channel coated with a lawn of two types of oligos. Hybridization is enabled by the first of the two types of oligos on the surface. This oligo is complementary to a first adapter on one end of the fragment. A polymerase creates a complement strand of the hybridized fragment. The double-stranded molecule is denatured, and the original template strand is washed away. The remaining strand, in parallel with many other remaining strands, is clonally amplified through bridge application.

In bridge amplification, a second adapter region on a second end of the strand hybridizes with the second type of oligos on the flow cell surface. A polymerase generates a complementary strand, forming a double-stranded bridge molecule. This double-stranded molecule is denatured resulting in two single-stranded molecules tethered to the flow cell through two different oligos. The process is then repeated over and over, and occurs simultaneously for millions of clusters resulting in clonal amplification of all the fragments. After bridge amplification, the reverse strands are cleaved and washed off, leaving only the forward strands. The 3' ends are blocked to prevent unwanted priming.

After clustering, sequencing starts with extending a first sequencing primer to generate the first read. With each cycle, fluorescently tagged nucleotides compete for addition to the growing chain. Only one is incorporated based on the sequence of the template. After the addition of each nucleotide, the cluster is excited by a light source, and a characteristic fluorescent signal is emitted. The number of cycles determines the length of the read. The emission wavelength and the signal intensity determine the base call. For a given cluster all identical strands are read simultaneously. Hundreds of millions of clusters are sequenced in a massively parallel manner. At the completion of the first read, the read product is washed away.

In the next step of protocols involving two index primers, an index 1 primer is introduced and hybridized to an index 1 region on the template. Index regions provide identification of fragments, which is useful for de-multiplexing samples in a multiplex sequencing process. The index 1 read is generated similar to the first read. After completion of the index 1 read, the read product is washed away and the 3' end of the strand is de-protected. The template strand then folds over and binds to a second oligo on the flow cell. An index 2 sequence is read in the same manner as index 1. Then an index 2 read product is washed off at the completion of the step.

After reading two indices, read 2 initiates by using polymerases to extend the second flow cell oligos, forming a double-stranded bridge. This double-stranded DNA is denatured, and the 3' end is blocked. The original forward strand is cleaved off and washed away, leaving the reverse strand. Read 2 begins with the introduction of a read 2 sequencing primer. As with read 1, the sequencing steps are repeated until the desired length is achieved. The read 2 product is washed away. This entire process generates millions of reads, representing all the fragments. Sequences from pooled sample libraries are separated based on the unique indices introduced during sample preparation. For each sample, reads of similar stretches of base calls are locally clustered. Forward and reversed reads are paired creating contiguous sequences. These contiguous sequences are aligned to the reference genome for variant identification.

The sequencing by synthesis example described above involves paired end reads, which is used in many of the embodiments of the disclosed methods. Paired end sequencing involves 2 reads from the two ends of a fragment. Paired end reads are used to resolve ambiguous alignments. Paired-end sequencing allows users to choose the length of the insert (or the fragment to be sequenced) and sequence either end of the insert, generating high-quality, alignable sequence data. Because the distance between each paired read is known, alignment algorithms can use this information to map reads over repetitive regions more precisely. This results in better alignment of the reads, especially across difficult-to-sequence, repetitive regions of the genome. Paired-end sequencing can detect rearrangements, including insertions and deletions (indels) and inversions.

Paired end reads may use insert of different length (i.e., different fragment size to be sequenced). As the default meaning in this disclosure, paired end reads are used to refer to reads obtained from various insert lengths. In some instances, to distinguish short-insert paired end reads from long-inserts paired end reads, the latter is specifically referred to as mate pair reads. In some embodiments involving mate pair reads, two biotin junction adaptors first are attached to two ends of a relatively long insert (e.g., several kb). The biotin junction adaptors then link the two ends of the insert to form a circularized molecule. A sub-fragment encompassing the biotin junction adaptors can then be obtained by further fragmenting the circularized molecule. The sub-fragment including the two ends of the original fragment in opposite sequence order can then be sequenced by the same procedure as for short-insert paired end sequencing described above. Further details of mate pair sequencing using an Illumina platform is shown in an online publication at the following address, which is incorporated by reference by its entirety: res.illumina.com/documents/products/technotes/technote_nextera_matepair_data_processing.pdf After sequencing of DNA fragments, sequence reads of predetermined length, e.g., 100 bp, are mapped or aligned to a known reference genome. The mapped or aligned reads and their corresponding locations on the reference sequence are also referred to as tags. The analyses of many embodiments disclosed herein for determining repeat expansion make use of reads that are either poorly aligned or cannot be aligned, as well as aligned reads (tags). In one embodiment, the reference genome sequence is the NCBI36/hg18 sequence, which is available on the world wide web at genome.ucsc.edu/cgi-bin/hgGateway?org=Human&db=hg18&hgsid=166260105). Alternatively, the reference genome sequence is the GRCh37/hg19, which is available on the world wide web at genome.ucsc.edu/cgi-bin/hgGateway. Other sources of public sequence information include GenBank, dbEST, dbSTS, EMBL (the European Molecular Biology Laboratory), and the DDBJ (the DNA Databank of Japan). A number of computer algorithms are available for aligning sequences, including without limitation BLAST (Altschul et al., 1990), BLITZ (MPsrch) (Sturrock & Collins, 1993), FASTA (Person & Lipman, 1988), BOWTIE (Langmead et al., Genome Biology 10:R25.1-R25.10 [2009]), or ELAND (Illumina, Inc., San Diego, CA, USA). In one embodiment, one end of the clonally expanded copies of the plasma cfDNA molecules is sequenced and processed by bioinformatic alignment analysis for the Illumina Genome Analyzer, which uses the Efficient Large-Scale Alignment of Nucleotide Databases (ELAND) software.

In one illustrative, but non-limiting, embodiment, the methods described herein comprise obtaining sequence information for the nucleic acids in a test sample, using single molecule sequencing technology of the Helicos True Single Molecule Sequencing (tSMS) technology (e.g. as described in Harris T. D. et al., Science 320:106-109 [2008]). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. In certain embodiments the templates can be at a density of about 100 million templates/cm$^2$. The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are discerned by imaging the flow cell surface. After imaging, a cleavage step removes the fluorescent label, and the process is repeated with other fluorescently labeled nucleotides until the desired read length is achieved. Sequence information is collected with each nucleotide addition step. Whole genome sequencing by single molecule sequencing technologies excludes or typically obviates PCR-based amplification in the preparation of the sequencing libraries, and the methods allow for direct measurement of the sample, rather than measurement of copies of that sample.

In another illustrative, but non-limiting embodiment, the methods described herein comprise obtaining sequence information for the nucleic acids in the test sample, using the 454 sequencing (Roche) (e.g. as described in Margulies, M. et al. Nature 437:376-380 [2005]). 454 sequencing typically involves two steps. In the first step, DNA is sheared into fragments of approximately 300-800 base pairs, and the fragments are blunt-ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (e.g., picoliter-sized wells). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is measured and analyzed.

In another illustrative, but non-limiting, embodiment, the methods described herein comprises obtaining sequence information for the nucleic acids in the test sample, using the SOLiD™ technology (Applied Biosystems). In SOLiD™ sequencing-by-ligation, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

In another illustrative, but non-limiting, embodiment, the methods described herein comprise obtaining sequence information for the nucleic acids in the test sample, using the single molecule, real-time (SMRT™) sequencing technology of Pacific Biosciences. In SMRT sequencing, the continuous incorporation of dye-labeled nucleotides is imaged during DNA synthesis. Single DNA polymerase molecules are attached to the bottom surface of individual zero-mode wavelength detectors (ZMW detectors) that obtain sequence information while phospholinked nucleotides are being incorporated into the growing primer strand. A ZMW detector comprises a confinement structure that enables observation of incorporation of a single nucleotide by DNA polymerase against a background of fluorescent nucleotides that rapidly diffuse in an out of the ZMW (e.g., in microseconds). It typically takes several milliseconds to incorporate a nucleotide into a growing strand. During this time, the fluorescent label is excited and produces a fluorescent signal, and the fluorescent tag is cleaved off. Measurement of the corresponding fluorescence of the dye indicates which base was incorporated. The process is repeated to provide a sequence.

In another illustrative, but non-limiting embodiment, the methods described herein comprise obtaining sequence information for the nucleic acids in the test sample, using nanopore sequencing (e.g. as described in Soni GV and Meller A. Clin Chem 53: 1996-2001 [2007]). Nanopore sequencing DNA analysis techniques are developed by a number of companies, including, for example, Oxford Nanopore Technologies (Oxford, United Kingdom), Sequenom, NABsys, and the like. Nanopore sequencing is a single-molecule sequencing technology whereby a single molecule of DNA is sequenced directly as it passes through a nanopore. A nanopore is a small hole, typically of the order of 1 nanometer in diameter. Immersion of a nanopore in a conducting fluid and application of a potential (voltage) across it results in a slight electrical current due to conduction of ions through the nanopore. The amount of current that flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore provides a read of the DNA sequence.

In another illustrative, but non-limiting, embodiment, the methods described herein comprises obtaining sequence information for the nucleic acids in the test sample, using the chemical-sensitive field effect transistor (chemFET) array (e.g., as described in U.S. Patent Application Publication No. 2009/0026082). In one example of this technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be discerned as a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

In another embodiment, the DNA sequencing technology is the Ion Torrent single molecule sequencing, which pairs semiconductor technology with a simple sequencing chemistry to directly translate chemically encoded information (A, C, G, T) into digital information (0, 1) on a semiconductor chip. In nature, when a nucleotide is incorporated into a strand of DNA by a polymerase, a hydrogen ion is released as a byproduct. Ion Torrent uses a high-density array of micro-machined wells to perform this biochemical process in a massively parallel way. Each well holds a different DNA molecule. Beneath the wells is an ion-sensitive layer and beneath that an ion sensor. When a nucleotide, for example a C, is added to a DNA template and is then incorporated into a strand of DNA, a hydrogen ion will be released. The charge from that ion will change the pH of the solution, which can be detected by Ion Torrent's ion sensor. The sequencer—essentially the world's smallest solid-state pH meter—calls the base, going directly from chemical information to digital information. The Ion personal Genome Machine (PGM™) sequencer then sequentially floods the chip with one nucleotide after another. If the next nucleotide that floods the chip is not a match. No voltage change will be recorded and no base will be called. If there are two identical bases on the DNA strand, the voltage will be double, and the chip will record two identical bases called. Direct detection allows recordation of nucleotide incorporation in seconds.

In another embodiment, the present method comprises obtaining sequence information for the nucleic acids in the test sample, using sequencing by hybridization. Sequencing-by-hybridization comprises contacting the plurality of polynucleotide sequences with a plurality of polynucleotide probes, wherein each of the plurality of polynucleotide probes can be optionally tethered to a substrate. The substrate might be flat surface comprising an array of known nucleotide sequences. The pattern of hybridization to the array can be used to determine the polynucleotide sequences present in the sample. In other embodiments, each probe is tethered to a bead, e.g., a magnetic bead or the like. Hybridization to the beads can be determined and used to identify the plurality of polynucleotide sequences within the sample.

In some embodiments of the methods described herein, the sequence reads are about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130 bp, about 140 bp, about 150 bp, about 200 bp, about 250 bp, about 300 bp, about 350 bp, about 400 bp, about 450 bp, or about 500 bp. It is expected that technological advances will enable single-end reads of greater than 500 bp enabling for reads of greater than about 1000 bp when paired end reads are generated. In some embodiments, paired end reads are used to determine repeat expansion, which comprise sequence reads that are about 20 bp to 1000 bp, about 50 bp to 500 bp, or 80 bp to 150 bp. In various embodiments, the paired end reads are used to evaluate a sequence having a repeat expansion. The sequence having the repeat expansion is longer than the reads. In some embodiments, the sequence having the repeat expansion is longer than about 100 bp, 500 bp, 1000 bp, or 4000 bp. Mapping of the sequence reads is achieved by comparing the sequence of the reads with the sequence of the reference to determine the chromosomal origin of the sequenced nucleic acid molecule, and specific genetic sequence information is not needed. A small degree of mismatch (0-2 mismatches per read) may be allowed to account for minor polymorphisms that may exist between the reference genome and the genomes in the mixed sample. In some embodiments, reads that are aligned to the reference sequence are used as anchor reads, and reads paired to anchor reads but cannot align or poorly align to the reference are used as anchored reads. In some embodiments, poorly aligned reads may have a relatively large number of percentage of mismatches per read, e.g., at least about 5%, at least about 10%, at least about 15%, or at least about 20% mismatches per read.

A plurality of sequence tags (i.e., reads aligned to a reference sequence) are typically obtained per sample. In some embodiments, at least about $3\times10^6$ sequence tags, at least about $5\times10^6$ sequence tags, at least about $8\times10^6$ sequence tags, at least about $10\times10^6$ sequence tags, at least about $15\times10^6$ sequence tags, at least about $20\times10^6$ sequence tags, at least about $30\times10^6$ sequence tags, at least about $40\times10^6$ sequence tags, or at least about $50\times10^6$ sequence tags of, e.g., 100 bp, are obtained from mapping the reads to the reference genome per sample. In some embodiments, all the sequence reads are mapped to all regions of the reference genome, providing genome-wide reads. In other embodiments, reads mapped to a sequence of interest, e.g., a chromosome, a segment of a chromosome, or a repeat sequence of interest.

Apparatus and Systems for Determining Repeat Expansion

Analysis of the sequencing data and the diagnosis derived therefrom are typically performed using various computer executed algorithms and programs. Therefore, certain embodiments employ processes involving data stored in or transferred through one or more computer systems or other processing systems. Embodiments disclosed herein also relate to apparatus for performing these operations. This apparatus may be specially constructed for the required purposes, or it may be a general-purpose computer (or a group of computers) selectively activated or reconfigured by a computer program and/or data structure stored in the computer. In some embodiments, a group of processors performs some or all of the recited analytical operations collaboratively (e.g., via a network or cloud computing) and/or in parallel. A processor or group of processors for performing the methods described herein may be of various types including microcontrollers and microprocessors such as programmable devices (e.g., CPLDs and FPGAs) and non-programmable devices such as gate array ASICs or general purpose microprocessors.

One embodiment provides a system for use in determining genotypes of variants at genomic loci including repeat sequences, the system including a sequencer for receiving a nucleic acid sample and providing nucleic acid sequence information from a sample; a processor; and a machine readable storage medium having stored thereon instructions for execution on said processor to genotype the variants by: (a) collecting nucleic acid sequence reads of the test sample from a database; (b) aligning the sequence reads to the one or more repeat sequences each represented by a sequence graph, wherein the sequence graph has a data structure of a directed graph with vertices representing nucleic acid sequences and directed edges connecting the vertices, and wherein the sequence graph comprises one or more self-loops, each self-loop representing a repeat sub-sequence, each repeat sub-sequence comprising repeats of a repeat unit of one or more nucleotides; and (c) determining one or more genotypes for the one or more repeat sequences using the sequence reads aligned to the one or more repeat sequences.

In some embodiments of any of the systems provided herein, the sequencer is configured to perform next generation sequencing (NGS). In some embodiments, the sequencer is configured to perform massively parallel sequencing using sequencing-by-synthesis with reversible dye terminators. In other embodiments, the sequencer is configured to perform sequencing-by-ligation. In yet other embodiments, the sequencer is configured to perform single molecule sequencing.

In addition, certain embodiments relate to tangible and/or non-transitory computer readable media or computer program products that include program instructions and/or data (including data structures) for performing various computer-implemented operations. Examples of computer-readable media include, but are not limited to, semiconductor memory devices, magnetic media such as disk drives, magnetic tape, optical media such as CDs, magneto-optical media, and hardware devices that are specially configured to store and perform program instructions, such as read-only memory devices (ROM) and random access memory (RAM). The computer readable media may be directly controlled by an end user or the media may be indirectly controlled by the end user. Examples of directly controlled media include the media located at a user facility and/or media that are not shared with other entities. Examples of indirectly controlled media include media that is indirectly accessible to the user via an external network and/or via a service providing shared resources such as the "cloud." Examples of program instructions include both machine code, such as produced by a compiler, and files containing higher level code that may be executed by the computer using an interpreter.

In various embodiments, the data or information employed in the disclosed methods and apparatus is provided in an electronic format. Such data or information may include reads and tags derived from a nucleic acid sample, reference sequences (including reference sequences providing solely or primarily polymorphisms), calls such as repeat expansion calls, counseling recommendations, diagnoses, and the like. As used herein, data or other information provided in electronic format is available for storage on a machine and transmission between machines. Conventionally, data in electronic format is provided digitally and may be stored as bits and/or bytes in various data structures, lists, databases, etc. The data may be embodied electronically, optically, etc.

One embodiment provides a computer program product for generating an output indicating the presence or absence of a repeat expansion in a test sample. The computer product may contain instructions for performing any one or more of the above-described methods for determining a repeat expansion. As explained, the computer product may include a non-transitory and/or tangible computer readable medium having a computer executable or compilable logic (e.g., instructions) recorded thereon for enabling a processor to determine anchored read and repeats in anchored reads, and whether a repeat expansion is present or absent. In one example, the computer product comprises a computer readable medium having a computer executable or compilable logic (e.g., instructions) recorded thereon for enabling a processor to diagnose a repeat expansion comprising: a receiving procedure for receiving sequencing data from at least a portion of nucleic acid molecules from a biological sample, wherein said sequencing data comprises paired end reads that have undergone alignment to a repeat sequence; computer assisted logic for analyzing a repeat expansion from said received data; and an output procedure for generating an output indicating the presence, absence or kind of said repeat expansion.

The sequence information from the sample under consideration may be mapped to chromosome reference sequences to identify paired end reads aligned to or anchored to a repeat sequence of interest and to identify a repeat expansion of the repeat sequence. In various embodiments, the reference sequences are stored in a database such as a relational or object database.

It should be understood that it is not practical, or even possible in most cases, for an unaided human being to perform the computational operations of the methods disclosed herein. For example, mapping a single 30 bp read from a sample to any one of the human chromosomes might require years of effort without the assistance of a computational apparatus. Of course, the problem is compounded because reliable repeat expansion calls generally require mapping thousands (e.g., at least about 10,000) or even millions of reads to one or more chromosomes.

In various implementations, raw sequence reads are aligned to one or more sequence graphs representing one or more sequence of interests. In various implementations, at least 10,000, 100,000, 500,000, 1,000,000, 5,000,000 or 10,000,000 reads are aligned to one or more sequence graphs. In various implementations, the one or more sequence graphs include at least 1, 2, 5, 10, 50, 100, 500, 1000, 5,000, 10,000, or 50,000 sequence graphs.

In some implementations, raw sequence reads are initially aligned to a reference genome to determine the genomic coordinates of the reads before a subset of the initially aligned reads are aligned to one or more sequence graphs representing one or more sequence of interests. In various implementations, at least 10,000, 100,000, 500,000, 1,000, 000, 5,000,000, 10,000,000, or 100,000,000 reads are initially aligned to a reference genome. In some implementations, initially aligned reads are realigned to sequence graphs to determine repeat expansions at numerous regions (each region corresponding to a sequence graph). The total number of reads that are realigned to sequence graphs during each invocation of an implementation can range from thousands to many millions of reads. In various implementations, at least 100, 500, 1,000, 5,000, 10,000, 50,000, 100,000, 500,000, 1,000,000, 5,000,000 or 10,000,000 reads are realigned to each sequence graph. In various implementations, the one or more sequence graphs include at least 1, 2, 5, 10, 50, 100, 500, 1000, 5,000, 10,000, or 50,000 sequence graphs.

The methods disclosed herein can be performed using a system for determining genotypes of variants at a genomic locus including a repeat sequence. The system may include: (a) a sequencer for receiving nucleic acids from the test sample providing nucleic acid sequence information from the sample; (b) a processor; and (c) one or more computer-readable storage media having stored thereon instructions for execution on said processor to genotype variants at genomic loci including repeat sequences. In some embodiments, the methods are instructed by a computer-readable medium having stored thereon computer-readable instructions for carrying out a method for identifying any repeat expansion. Thus one embodiment provides a computer program product including a non-transitory machine readable medium storing program code that, when executed by one or more processors of a computer system, causes the computer system to implement a method for identifying a repeat expansion of a repeat sequence in a test sample including nucleic acids, wherein the repeat sequence includes repeats of a repeat unit of nucleotides. The program code may include: (a) code for collecting sequence reads of a test sample from a database; (b) code for aligning the sequence reads to the one or more repeat sequences each represented by a sequence graph, wherein the sequence graph has a data structure of a directed graph with vertices representing nucleic acid sequences and directed edges connecting the vertices, and wherein the sequence graph comprises one or more self-loops, each self-loop representing a repeat sub-sequence, each repeat sub-sequence comprising repeats of a repeat unit of one or more nucleotides; and (c) code for determining one or more genotypes for the one or more repeat sequences using the sequence reads aligned to the one or more repeat sequences.

In some embodiments, the instructions may further include automatically recording information pertinent to the method such as repeats and anchored reads, and the presence or absence of a repeat expansion in a patient medical record for a human subject providing the test sample. The patient medical record may be maintained by, for example, a laboratory, physician's office, a hospital, a health maintenance organization, an insurance company, or a personal medical record website. Further, based on the results of the processor-implemented analysis, the method may further involve prescribing, initiating, and/or altering treatment of a human subject from whom the test sample was taken. This may involve performing one or more additional tests or analyses on additional samples taken from the subject.

Disclosed methods can also be performed using a computer processing system which is adapted or configured to perform a method for identifying any repeat expansions. One embodiment provides a computer processing system which is adapted or configured to perform a method as described herein. In one embodiment, the apparatus includes a sequencing device adapted or configured for sequencing at least a portion of the nucleic acid molecules in a sample to obtain the type of sequence information described elsewhere herein. The apparatus may also include components for processing the sample. Such components are described elsewhere herein.

Sequence or other data, can be input into a computer or stored on a computer readable medium either directly or indirectly. In one embodiment, a computer system is directly coupled to a sequencing device that reads and/or analyzes sequences of nucleic acids from samples. Sequences or other information from such tools are provided via interface in the computer system. Alternatively, the sequences processed by system are provided from a sequence storage source such as a database or other repository. Once available to the processing apparatus, a memory device or mass storage device buffers or stores, at least temporarily, sequences of the nucleic acids. In addition, the memory device may store tag counts for various chromosomes or genomes, etc. The memory may also store various routines and/or programs for analyzing the presenting the sequence or mapped data. Such programs/routines may include programs for performing statistical analyses, etc.

In one example, a user provides a sample into a sequencing apparatus. Data is collected and/or analyzed by the sequencing apparatus which is connected to a computer. Software on the computer allows for data collection and/or analysis. Data can be stored, displayed (via a monitor or other similar device), and/or sent to another location. The computer may be connected to the internet which is used to transmit data to a handheld device utilized by a remote user (e.g., a physician, scientist or analyst). It is understood that the data can be stored and/or analyzed prior to transmittal. In some embodiments, raw data is collected and sent to a remote user or apparatus that will analyze and/or store the data. Transmittal can occur via the internet, but can also occur via satellite or other connection. Alternately, data can be stored on a computer-readable medium and the medium can be shipped to an end user (e.g., via mail). The remote user can be in the same or a different geographical location including, but not limited to a building, city, state, country or continent.

In some embodiments, the methods also include collecting data regarding a plurality of polynucleotide sequences (e.g., reads, tags and/or reference chromosome sequences) and sending the data to a computer or other computational system. For example, the computer can be connected to laboratory equipment, e.g., a sample collection apparatus, a nucleotide amplification apparatus, a nucleotide sequencing apparatus, or a hybridization apparatus. The computer can then collect applicable data gathered by the laboratory device. The data can be stored on a computer at any step, e.g., while collected in real time, prior to the sending, during or in conjunction with the sending, or following the sending. The data can be stored on a computer-readable medium that can be extracted from the computer. The data collected or stored can be transmitted from the computer to a remote location, e.g., via a local network or a wide area network such as the internet. At the remote location various operations can be performed on the transmitted data as described below.

Among the types of electronically formatted data that may be stored, transmitted, analyzed, and/or manipulated in systems, apparatus, and methods disclosed herein are the following:
  Reads obtained by sequencing nucleic acids in a test sample
  Tags obtained by aligning reads to a reference genome or other reference sequence or sequences
  The reference genome or sequence
  Locus specification indicating locus identity, location, and structure
  Read coverage
  Genotype of variants
  Sequence graph
  Graph paths
  Graph alignment information
  The actual calls of repeat expansion
  Diagnoses (clinical condition associated with the calls)
  Recommendations for further tests derived from the calls and/or diagnoses
  Treatment and/or monitoring plans derived from the calls and/or diagnoses These various types of data may be obtained, stored transmitted, analyzed, and/or manipulated at one or more locations using distinct apparatus. The processing options span a wide spectrum. At one end of the spectrum, all or much of this information is stored and used at the location where the test sample is processed, e.g., a doctor's office or other clinical setting. In other extreme, the sample is obtained at one location, it is processed and optionally sequenced at a different location, reads are aligned and calls are made at one or more different locations, and diagnoses, recommendations, and/or plans are prepared at still another location (which may be a location where the sample was obtained).

In various embodiments, the reads are generated with the sequencing apparatus and then transmitted to a remote site where they are processed to produce repeat expansion calls. At this remote location, as an example, the reads are aligned to a reference sequence to produce anchor and anchored reads. Among the processing operations that may be employed at distinct locations are the following:
  Sample collection
  Sample processing preliminary to sequencing
  Sequencing
  Analyzing sequence data and deriving repeat expansion calls
  Diagnosis
  Reporting a diagnosis and/or a call to patient or health care provider
  Developing a plan for further treatment, testing, and/or monitoring
  Executing the plan
  Counseling Any one or more of these operations may be automated as described elsewhere herein. Typically, the sequencing and the analyzing of sequence data and deriving repeat expansion calls will be performed computationally. The other operations may be performed manually or automatically.

Figure 6:
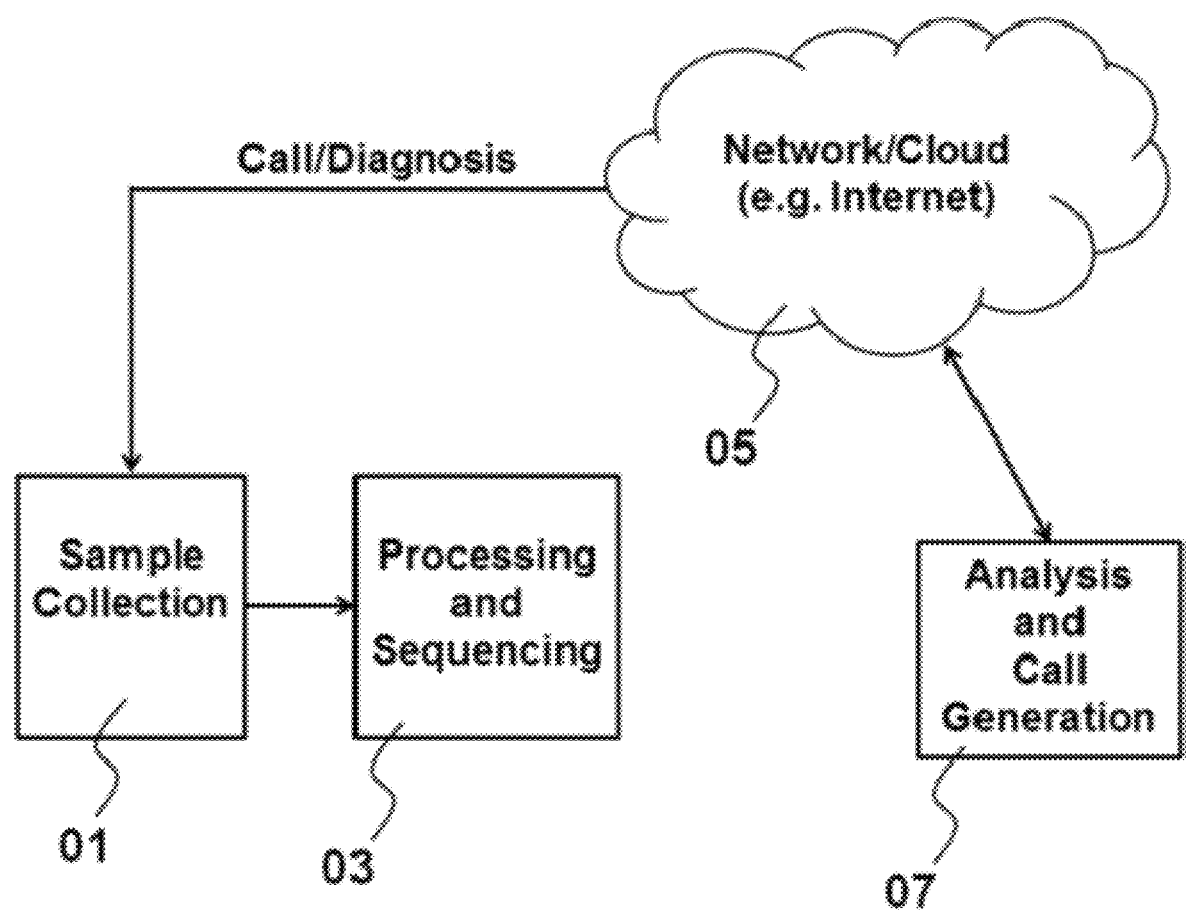
FIG. 6 is a block diagram of a dispersed system for processing a test sample.
Figure 7A:
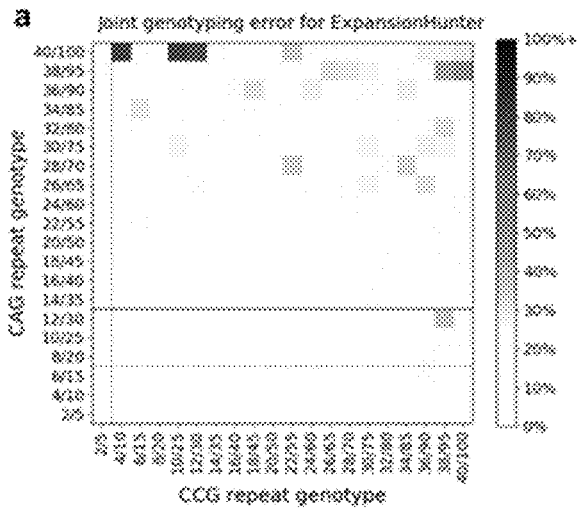
FIGS. 7A, 7B, 7C, and 7D show accuracy of genotyping CAG and CCG STRs in the HTT locus from simulated data using different methods.
Figure 7B:
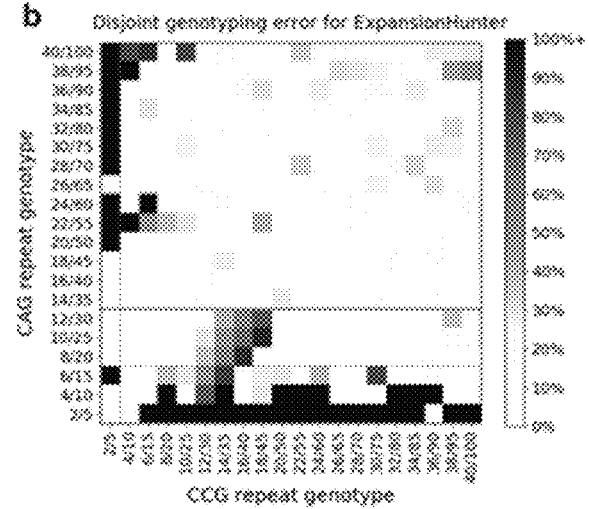
Figure 7C:
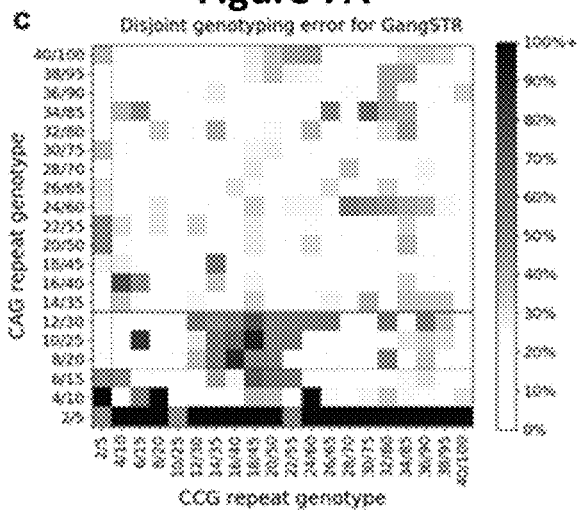
Figure 7D:
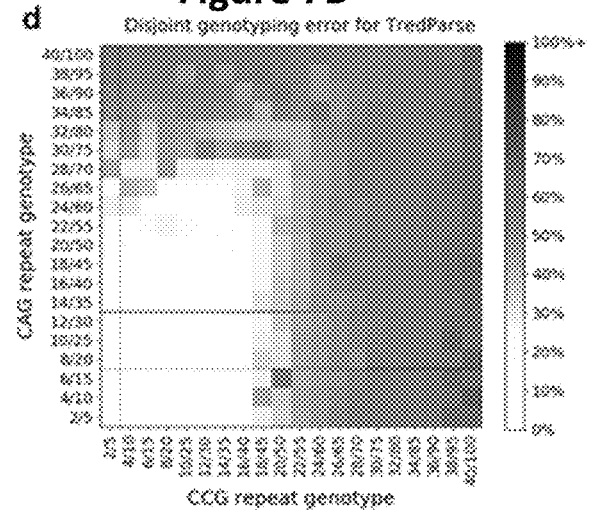

FIG. 6 shows one implementation of a dispersed system for producing a call or diagnosis from a test sample. A sample collection location 01 is used for obtaining a test sample from a patient. The samples then provided to a processing and sequencing location 03 where the test sample may be processed and sequenced as described above. Location 03 includes apparatus for processing the sample as well as apparatus for sequencing the processed sample. The result of the sequencing, as described elsewhere herein, is a collection of reads which are typically provided in an electronic format and provided to a network such as the Internet, which is indicated by reference number 05 in FIG. 6.

The sequence data is provided to a remote location 07 where analysis and call generation are performed. This location may include one or more powerful computational devices such as computers or processors. After the computational resources at location 07 have completed their analysis and generated a call from the sequence information received, the call is relayed back to the network 05. In some implementations, not only is a call generated at location 07 but an associated diagnosis is also generated. The call and or diagnosis are then transmitted across the network and back to the sample collection location 01 as illustrated in FIG. 6. As explained, this is simply one of many variations on how the various operations associated with generating a call or diagnosis may be divided among various locations. One common variant involves providing sample collection and processing and sequencing in a single location. Another variation involves providing processing and sequencing at the same location as analysis and call generation.

EXPERIMENTAL

Examples

We applied the program to a simulated dataset containing a wide range of CAG and CCG repeat sizes at the HTT locus. HTT or Huntingtin is a disease gene linked to Huntington's disease (HD), a neurodegenerative disorder characterized by loss of striatal neurons. This is thought to be caused by an expanded, unstable trinucleotide repeat in the huntingtin gene, which translates as a polyglutamine repeat in the protein product. A fairly broad range of trinucleotide repeats (9-35) has been identified in normal controls, and repeat numbers in excess of 40 have been described as pathological.

As expected, the accuracy obtained using methods according to some implementations was substantially higher when the reads were aligned to sequence graph containing both repeats compared to when both repeats were analyzed independently. We observed similar improvement compared to other STR genotyping tools that were not designed to handle loci harboring multiple nearby STRs (See FIGS. 7A, 7B, 7C, and 7D).

To demonstrate that the implementations can genotype degenerate DNA repeats, we analyzed a polyalanine repeat in PHOX2B gene in 150 healthy controls and one sample harboring a known pathogenic expansion. PHOX2B contains a polyalanine repeat of 20 codons that can expand to cause congenital central hypoventilation syndrome. Consistent with what is known about this repeat (Amiel et al. 2003), all but a few controls were genotyped 20/20. The implementations accurately genotyped the sole sample with the expansion as 20/27; the correctness of this genotype was confirmed by Sanger sequencing. The implementations also correctly detected the pathogenic SNV adjacent to an adenosine homopolymer in the MSH2 gene in three WGS replicates of a sample obtained from SeraCare Life Sciences (see Supplementary Materials).

In summary, we have developed a novel method that addresses the need for more accurate genotyping of complex loci. This method can genotype polyalanine repeats and resolve difficult regions containing repeats in close proximity to small variants and other repeats. We expect that the flexibility of the sequence graph framework now adopted in the implementations will enable a variety of novel variant calling applications.

Analysis of CAG and CCG STRs in the HTT Locus

We simulated a short read sample for each combination of CAG and CCG repeat genotypes using wgsim (Li, n.d.). We set the read length to 150, distance between mate ends to 350, standard deviation for mate end distance to 50, rate of mutations and base error rate to 0.0010, and fraction of indels to 0. The number of pairs was set to yield 40× coverage of the locus. The reads were aligned to GRCh37 reference with BWA-MEM 0.7.17-r1194-dirty (Li 2013).

We analyzed these data with some implementations in two ways. First, we specified the structure of the HTT locus using the expression (CAG)*CAACAG(CCG)* ensuring that reads are aligned to the sequence graph containing both repeats. Then we used some implementations to analyze each repeat independently. In this mode, the reads were aligned to the graph representing the CAG STR and, separately, to the graph representing CCG STR. Finally we analyzed both repeats independently with the latest versions of GangSTR and TredParse that do not use sequence graphs to align reads to the repeat region (FIGS. 7A, 7B, 7C, and 7D).

FIGS. 7A, 7B, 7C, and 7D show accuracy of genotyping CAG and CCG STRs in the HTT locus from simulated data. (a) Performance of an implementation when reads are aligned to sequence graph containing both repeats; (b) performance of an implementation when repeats are analyzed independently; (c) performance of GangSTR; (d) performance of TredParse. For each simulated sample, we measured the maximum percentage deviation of the predicted STR lengths from the expected STR lengths. Dotted blue lines correspond to the genotype in the reference genome and solid red lines represent the threshold for pathogenic expansions. The implementation accurately predicts the correct genotypes for all samples when genotyping both repeats jointly. Joint genotyping provided a high advantage over separately genotyping both repeats with any of the three tools which showed a high relative error rate especially when one of the repeats was significantly longer than the other.

Datasets

The PCR-free WGS sequencing data for 150 unrelated controls used for the analysis of the PHOX2B polyalanine repeat is the Polaris Diversity Cohort. It consists of samples selected from the International Genome Sample Resource (1000 Genomes Project Consortium et al. 2015) (www1.linternationalgenome1.lorg/). The WGS data can be obtained from European Genome-phenome Archive (EGA; www1.lebil.lacl.luk/ega/home; PRJEB20654) and from NCBI Sequence Read Archive (SRA; www1.lncbil.lnlml.lnihl.lgov/sra; bioproject:387148). The description of the samples (githubl.lcom/Illumina/Polaris/wiki/HiSeqX-Diversity-Cohort).

The sample with the 20/27 expansion in PHOX2B was obtained from the Genetics Laboratories Molecular Genetics, Addenbrooke's Treatment Centre, and Cambridge University.

The SeraCare Life Sciences sample, Seraseq Inherited Cancer DNA Mix v1, contains variants that are known to be both pathogenic and hard-to-call. The variants have been synthetically added to the well-characterized cell line GM24385, all with expected variant frequencies of 50%. One of these engineered mutations corresponds to an SNV in the MSH2 gene, which is directly adjacent to a long homopolymer A region.

Three replicates of the SeraCare sample were prepared with the Illumina TruSeq PCR Free kit. The replicates were run on a single lane of the NovaSeq6000 using the XP workflow and sequenced at 2×151 read length. The replicates were analyzed using the 'Sentieon DNASeq FASTQ to VCF' and 'Whole Genome Resequencing v8.0.0' Basespace apps (https://basespace.illumina.com). Sentieon can be regarded as proxy for variant calling performance of the Broad's BWA-GATK software suite as Sentieon implements the same algorithms. Neither of the software solutions was able to correctly identify the MSH2 SNV. Fastq files and analysis results are provided through Basespace: https://basespace.illumina.com/s/HAQNxJyEULP The present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope

What is claimed is:

1. A method, implemented using a computer comprising one or more processors and system memory, for genotyping one or more repeat sequences each including one or more repeat sub-sequences, the method comprising:
   (a) collecting, using the one or more processors, sequence reads of a test sample from a database, wherein the sequence reads have a length of at least 100 base pairs;
   (b) aligning, by the one or more processors, the sequence reads to a reference sequence that spans the one or more repeat sequences each represented by a sequence graph, wherein the sequence graph has a data structure of a directed graph with vertices representing nucleic acid sequences and directed edges connecting the vertices, and wherein the sequence graph comprises one or more self-loops, each self-loop representing a repeat sub-sequence, each repeat sub-sequence comprising repeats of a repeat unit of one or more nucleotides, wherein the reference sequence is at least about 2000 base pairs, and wherein the number of sequence reads aligned is at least 100; and
   (c) determining, by the one or more processors, one or more genotypes for the one or more repeat sequences using the sequence reads aligned to the one or more repeat sequences.

2. The method of claim 1, wherein a repeat sequence of the one or more repeat sequences comprises a particular repeat unit comprising at least one incompletely specified nucleotide.

3. The method of claim 2, wherein the particular repeat unit comprises degenerate codons.

4. The method of claim 1, wherein the one or more self-loops comprise two or more self-loops representing two or more repeat sub-sequences.

5. The method of claim 1, wherein the sequence graph further comprises two or more alternative paths for two or more alleles.

6. The method of claim 5, wherein the two or more alleles comprise an indel or a substitution.

7. The method of claim 5, wherein the substitution comprises a single nucleotide variant (SNV) or a single nucleotide polymorphism (SNP).

8. The method of claim 5, further comprising genotyping the two or more alleles using sequence reads aligned to the two or more alternative paths.

9. The method of claim 8, wherein genotyping the two or more alleles comprises providing coverages of the two or more alternative paths to a probabilistic model to determine the probabilities of the two or more alleles.

10. The method of claim 9, wherein the probabilistic model simulates a probability of an allele as a function of the coverage of the allele, the function being selected from a Poisson distribution, negative-binomial distribution, a binomial distribution, or a beta-binomial distribution.

11. The method of claim 1, further comprising, aligning, before (b), the sequence reads to a reference genome to determine genomic coordinates of the sequence reads, and selecting a subset of sequence reads as the sequence reads to be aligned to the one or more repeat sequences each represented by a sequence graph.

12. The method of claim 1, wherein aligning a sequence read to the sequence graph comprises:
   finding a kmer match between the sequence read and a path of the sequence graph; and
   extending the kmer match to a full alignment of nodes and edges of the sequence graph including one or more self-loops.

13. The method of claim 1, wherein aligning a sequence read to the sequence graph comprises graph shrinking by removing low confidence ends of the alignments.

14. The method of claim 1, wherein aligning a sequence read to the sequence graph comprises alignment merging by:
   aligning subsequences of the read to a sequence graph; and
   merging alignments of the subsequences to form a full alignment of the sequence read.

15. The method of claim 1, further comprising generating the sequence graph based on locus specification comprising a locus structure of the genomic locus.

16. The method of claim 1, wherein the sequence reads comprise paired end reads, and operation (c) comprises:
   (i) identifying anchor and anchored reads in the paired end reads, wherein the anchor reads are reads aligned to or near the one or more repeat sequences, and the anchored reads are unaligned reads that are paired with the anchor reads; and
   (ii) determining the one or more genotypes for the one or more repeat sequences using at least the anchored reads.

17. The method of claim 1, wherein the one or more repeat sequences comprise a short tandem repeat (STR) sequence.

18. The method of claim 17, wherein an expansion of the STR is associated with Fragile X syndrome, amyotrophic lateral sclerosis (ALS), Huntington's disease, Friedreich's ataxia, spinocerebellar ataxia, spino-bulbar muscular atrophy, myotonic dystrophy, Machado-Joseph disease, or dentatorubral pallidoluysian atrophy.

19. The method of claim 1, wherein each repeat sequence of the one or more repeat sequences are at least an order of magnitude longer in length than each of the sequence reads.

20. The method of claim 1, further comprising initially aligning the sequence reads to a reference genome to determine genomic coordinates of the sequence reads prior to aligning the sequence reads to the one or more repeat sequences in (b), wherein the reference genome includes the one or more repeat sequences.

21. The method of claim 20, wherein the reference genome is at least one of: at least 100 times larger than each of the sequence reads, or is a reference genome corresponding to a human chromosome.

22. A system comprising:
   system memory; and
   one or more processors configured to:
   (a) collect sequence reads of a test sample from a database, wherein the sequence reads have a length of at least 100 base pairs;

(b) align the sequence reads to a reference sequence that spans the one or more repeat sequences each represented by a sequence graph, wherein the sequence graph has a data structure of a directed graph with vertices representing nucleic acid sequences and directed edges connecting the vertices, and wherein the sequence graph comprises one or more self-loops, each self-loop representing a repeat sub-sequence, each repeat sub-sequence comprising repeats of a repeat unit of one or more nucleotides, wherein the reference sequence is at least about 2000 base pairs, and wherein the number of sequence reads aligned is at least 100; and (c) determine one or more genotypes for the one or more repeat sequences using the sequence reads aligned to the one or more repeat sequences.

23. A computer program product comprising a non-transitory machine readable medium storing program code that, when executed by one or more processors of a computer system, causes the computer system to implement a method for genotyping a repeat sequence in a test sample comprising nucleic acids, said program code comprising:

(a) code for collecting sequence reads of a test sample from a database, wherein the sequence reads have a length of at least 100 base pairs;

(b) code for aligning the sequence reads to a reference sequence that spans the one or more repeat sequences each represented by a sequence graph, wherein the sequence graph has a data structure of a directed graph with vertices representing nucleic acid sequences and directed edges connecting the vertices, and wherein the sequence graph comprises one or more self-loops, each self-loop representing a repeat sub-sequence, each repeat sub-sequence comprising repeats of a repeat unit of one or more nucleotides, wherein the reference sequence is at least about 2000 base pairs, and wherein the number of sequence reads aligned is at least 100; and (c) code for determining one or more genotypes for the one or more repeat sequences using the sequence reads aligned to the one or more repeat sequences.

* * * * *

```
                        SEQUENCE LISTING

<160> NUMBER OF SEQ ID NOS: 5

<210> SEQ ID NO 1
<211> LENGTH: 12
<212> TYPE: DNA
<213> ORGANISM: Artificial Sequence
<220> FEATURE:
<223> OTHER INFORMATION: Synthesized

<400> SEQUENCE: 1
cagcaacagc cg                                                          12

<210> SEQ ID NO 2
<211> LENGTH: 12
<212> TYPE: DNA
<213> ORGANISM: Artificial Sequence
<220> FEATURE:
<223> OTHER INFORMATION: Synthesized

<400> SEQUENCE: 2
cagcaacagc gg                                                          12

<210> SEQ ID NO 3
<211> LENGTH: 14
<212> TYPE: DNA
<213> ORGANISM: Artificial Sequence
<220> FEATURE:
<223> OTHER INFORMATION: Synthesized

<400> SEQUENCE: 3
tcgtcggcag cgtc                                                        14

<210> SEQ ID NO 4
<211> LENGTH: 15
<212> TYPE: DNA
<213> ORGANISM: Artificial Sequence
<220> FEATURE:
<223> OTHER INFORMATION: Synthesized

<400> SEQUENCE: 4
cagcagcagc agcag                                                       15

<210> SEQ ID NO 5
<211> LENGTH: 15
<212> TYPE: DNA
<213> ORGANISM: Artificial Sequence
<220> FEATURE:
<223> OTHER INFORMATION: Synthesized
```

```
<400> SEQUENCE: 5
ccgccgccgc cgccg                                                              15
```